(12) United States Patent
Haensler et al.

(10) Patent No.: US 8,506,971 B2
(45) Date of Patent: Aug. 13, 2013

(54) METHOD FOR ADJUVANTING LIPOPOLYSACCHARIDE (LPS) OF GRAM-NEGATIVE BACTERIA

(75) Inventors: Jean Haensler, Grezieu la Varenne (FR); Bruno Guy, Lyons (FR)

(73) Assignee: Sanofi Pasteur S.A., Lyons (FR)

( * ) Notice: Subject to any disclaimer, the term of this patent is extended or adjusted under 35 U.S.C. 154(b) by 184 days.

(21) Appl. No.: 12/780,388

(22) Filed: May 14, 2010

(65) Prior Publication Data
US 2011/0014272 A1 Jan. 20, 2011

Related U.S. Application Data

(60) Provisional application No. 61/229,577, filed on Jul. 29, 2009.

(30) Foreign Application Priority Data

May 14, 2009 (FR) .................................. 09 02330

(51) Int. Cl.
| | | |
|---|---|---|
| *A61K 45/00* | (2006.01) | |
| *A61K 39/385* | (2006.01) | |
| *A61K 39/02* | (2006.01) | |
| *A61K 39/095* | (2006.01) | |
| *A01N 25/26* | (2006.01) | |

(52) U.S. Cl.
USPC .................. 424/282.1; 424/193.1; 424/250.1; 424/234.1; 424/417; 424/418

(58) Field of Classification Search
None
See application file for complete search history.

(56) References Cited

U.S. PATENT DOCUMENTS

| 6,326,350 B1 | 12/2001 | Jacobs et al. |
| 6,531,131 B1 | 3/2003 | Gu |
| 2003/0059444 A1 | 3/2003 | Zollinger |

FOREIGN PATENT DOCUMENTS

| EP | 586 226 | 3/1994 |
| EP | 941 738 | 9/1999 |
| WO | 87/07297 | 12/1987 |
| WO | 98/31393 | 7/1998 |
| WO | 00/25811 | 5/2000 |
| WO | 00/66791 | 11/2000 |
| WO | 2006/108586 | 10/2006 |

OTHER PUBLICATIONS

Holst et al, Vaccine (2005) 23:2201.
Spohn et al., Vaccine (Jun. 2004) 22:2494.
Petrov et al., Infection and Immunity (1992) 60(9):3897.
Guy, Nature Reviews Microbiol. (2007) 5:505.
Chiavolini et al., Clin. Vaccine Immunol. (2008) 15(9)-1322.
Chen et al., "A novel technology for the production of a heterologous lipoprotein immunogen in high yield has implications for the field of vaccine design," Vaccine 27 (2009) 1400-1409.
Pavliakova et al., I&I (1999) 67(10):5526.
Braun et al., Vaccine (2004) 22:898.
Choudhury et al., Carbohydr. Res. (2008) 343:2971.
Mistretta et al., (2008) Poster at the 16th International Pathogenic Neisseria Conference, Rotterdam.
Wakarchuk et al., Eur. J. Biochem. (1998) 254:626.
Gamian et al., J.Biol.Chem. (1992) 267:922.
Kogan et al., Carbohydr. Res. (1997) 298:191.
Di Fabio et al., Can J. Chem. (1990) 68:1029.
Micron et al., J. Biol. Chem. (1990) 265:7243.
Michon et al., J. Biol. Chem. (2000) 275:9716.
Zhu et al., FEMS Microbiol. Letters (2001) 203:173.
Gu et al., J.Clin.Microbiol. (1992) 30(8):2047.
Westphal & Jann, Meth. Carbohydr. Chem. (1965) 5:88.
Wu et al., Anal. Biochem. (1987) 160:281.
Gu & Tsai, I&I (1993) 61:1873.
Tettelin et al., Science (Mar. 2000) 287:1809.
Parkhill et al., Nature (Mar. 2000) 404:502.
Bentley et al., PLoS Genet (2007) 3 e23.
Gupta et al., I&I (1992) 60(8):3201.
Gu et al., I&I (1996) 64(10):4047.
Trent et al., J. Biol. Chem. (2001) 276:9083.
Reynolds et al., J. Biol. Chem. (1987) 281:21974.
Steeghs et al., Cell. Microbiol. (2002) 4(9):599.
Muller-Loennies et al., J. Endotox. Res. (2002) 8(4):295.
Mieszala et al., Carbohydr. Res (2003) 338:167.
Cox et al., Vaccine (2005) 23(5):5045.
Wu et al., Vaccine (2005) 23:5177.
Taha et al., "*Neisseria meningitides*: Biological new," Revue Francophone Des Laboratoires, Feb. 2009, Supplement No. 409; pp. 36-38.

*Primary Examiner* — S. Devi
(74) *Attorney, Agent, or Firm* — McDonnell Boehnen Hulbert & Berghoff LLP

(57) ABSTRACT

The subject of the invention is a method for adjuvanting LPS of a Gram-negative bacterium, according to which LPS or LPS liposomes (LPS formulated in liposomes) is (are) mixed with the lipidated human-transferrin receptor subunit B (TbpB protein) of *Neisseria meningitidis* or a lipidated fragment thereof; or (ii) LPS and the lipidated TbpB of *N. meningitidis* or a lipidated fragment thereof are formulated together in liposomes; or (iii) LPS is conjugated with the lipidated TbpB of *N. meningitidis* or a lipidated fragment thereof; in order to obtain a preparation which does not contain OMVs and which is capable of inducing, after administration to a mammal, an anti-LPS immune response which is improved by comparison with the anti-LPS immune response observed after administration of the corresponding preparation in which the lipidated TbpB of *N. meningitidis* or a lipidated fragment thereof is omitted; as well as vaccine compositions thereof. The LPS may, for example, be the LOS of a non-enteric Gram-negative bacterium such as *N. meningitidis*.

8 Claims, 8 Drawing Sheets

Figure 1:
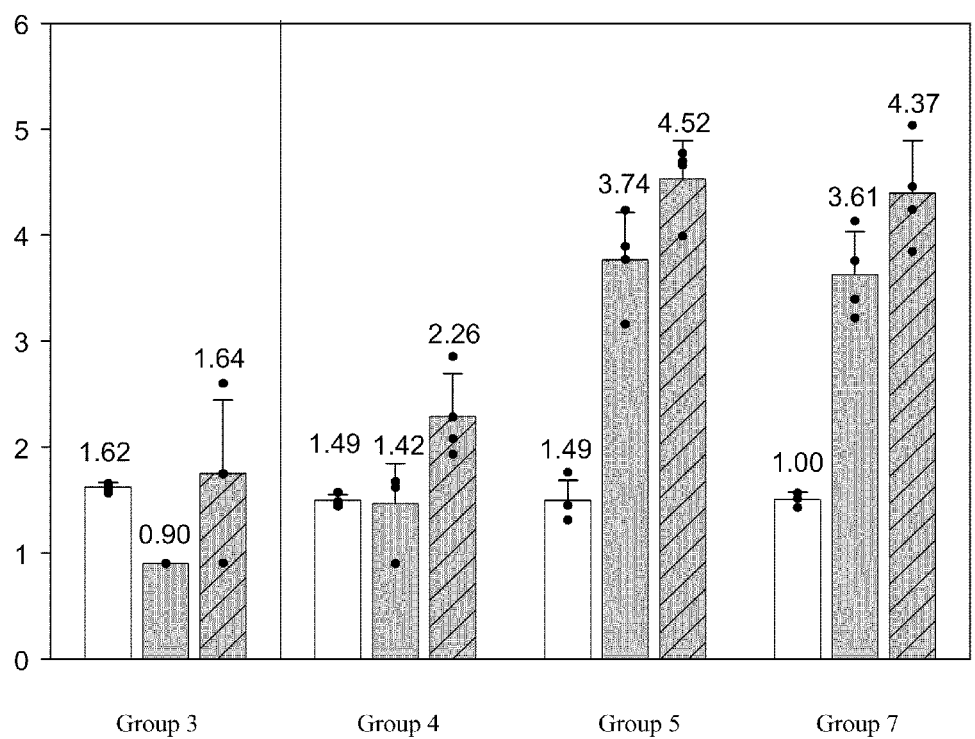

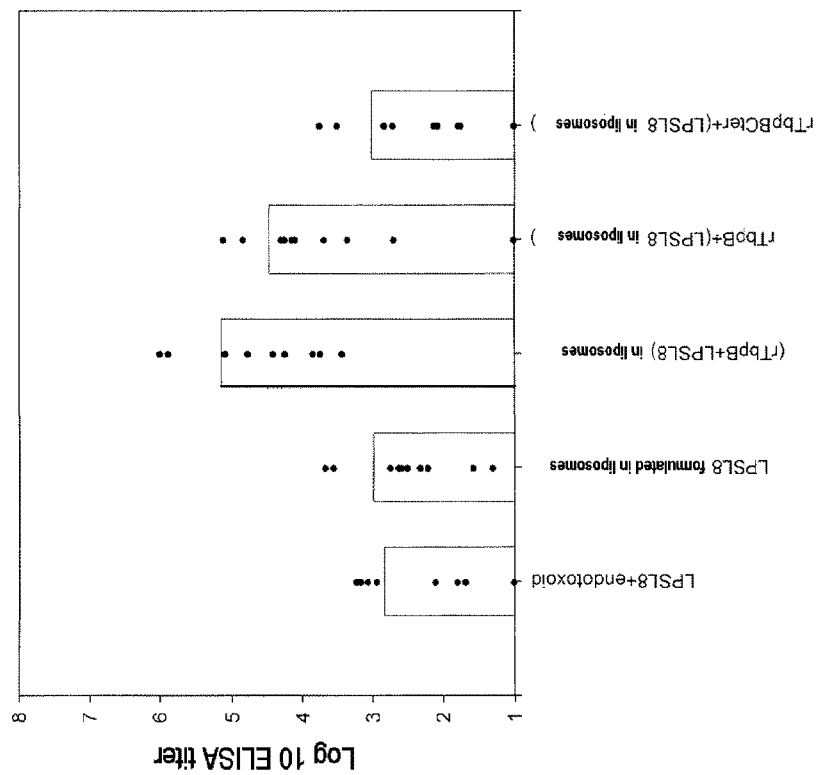
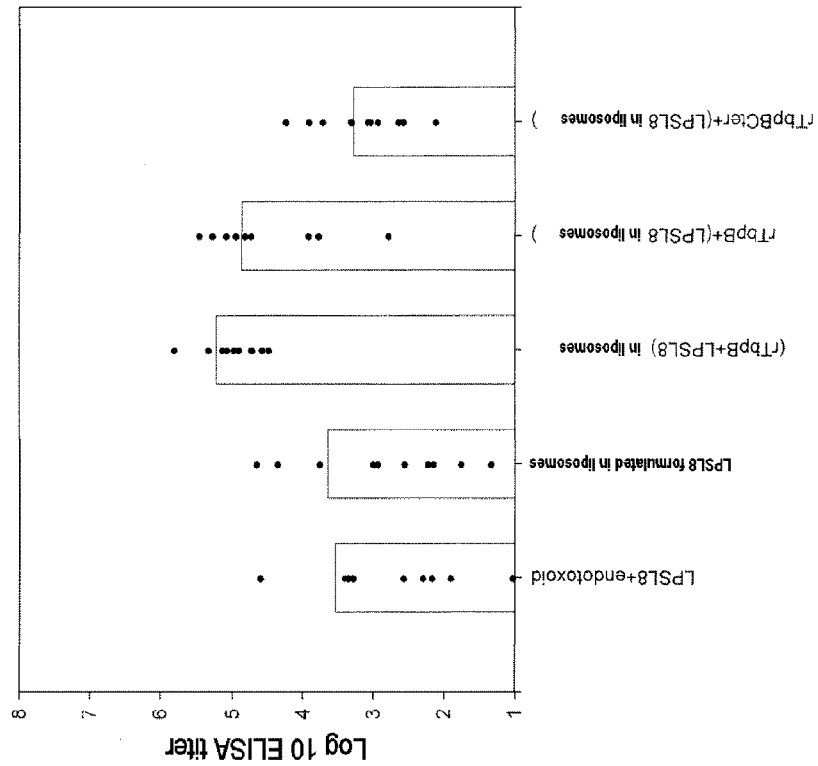

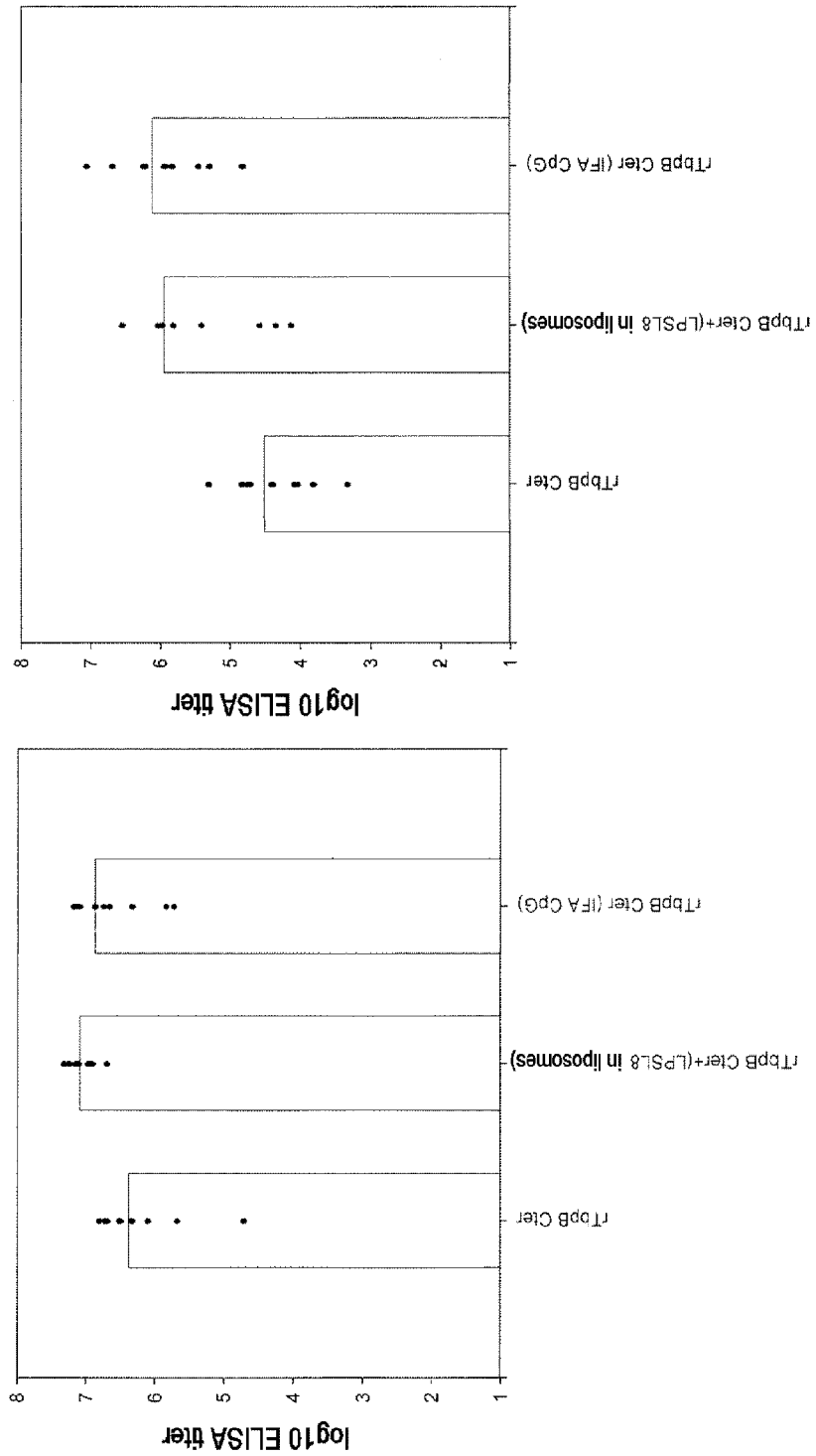

METHOD FOR ADJUVANTING LIPOPOLYSACCHARIDE (LPS) OF GRAM-NEGATIVE BACTERIA

This application is a nonprovisional application which claims priority to U.S. Provisional Patent Application Ser. No. 61/229,577 filed on Jul. 29, 2009, the disclosure of which is incorporated herein by reference.

The invention lies within the vaccine field and relates to a method for increasing the immune response of a mammal against a vaccine antigen of interest: a lipopolysaccharide (LPS) from Gram-negative bacteria.

LPS is a major constituent of the outer membrane of the wall of Gram-negative bacteria. LPS is toxic at high doses to mammals and, in view of this biological activity, has been called an endotoxin. It is responsible for septic shock, a fatal pathology which develops following acute infection with a Gram-negative bacterium.

The structure of LPS is constituted of a lipid portion, called lipid A, covalently bonded to a polysaccharide portion.

Lipid A is responsible for the toxicity of LPS. It is highly hydrophobic and enables the LPS to be anchored in the outer membrane of the wall. Lipid A is composed of a disaccharide structure substituted with fatty acid chains. The number and the composition of the fatty acid chains varies from one species to the other.

The polysaccharide portion is constituted of carbohydrate chains which are responsible for the antigenicity. At least 3 major regions can be distinguished in this polysaccharide portion:
(i) an inner core constituted of monosaccharides [one or more KDO (2-keto-3-deoxyoctulosonic acid) and one or more heptosis (Hep)] which are invariant within the same bacterial species;
(ii) an outer core bonded to heptose and constituted of various monosaccharides; and
(iii) an O-specific outer chain constituted of a series of repeating units—these repeating units themselves being composed of one or more different monosaccharides.

The composition of the polysaccharide portion varies from one species to another, from one serotype (immunotype in meningococcus) to another within the same species.

In a certain number of nonenteric Gram-negative bacteria such as *Neisseriae, Bordetellae, Branhamellas, Haemophilus* and *Moraxellae*, the O-specific chain does not exist. The LPS saccharide portion of these bacteria is constituted only of the oligosaccharide core. Consequently, the LPS from these bacteria is often called lipooligosaccharide (LOS).

LPS is not only toxic, it is also immunogenic. In mammals, anti-LPS antibodies are generated during carrying and infection and can be protective. Thus, the use of LPS has already been envisioned in the prophylaxis of infections due to Gram-negative bacteria and associated diseases.

LPS is not the only constituent of Gram-negative bacteria to have been proposed as a vaccine antigen. Certain proteins of these bacteria have likewise been proposed, and in particular certain proteins of the outer membrane thereof.

A convenient means for obtaining a vaccine composition consists in preparing OMVs (outer membrane vesicles) by treating blebs of a bacterial preparation with a detergent (octylglucoside). OMVs have many constituents: inter alia, residual LPS and the outer membrane proteins. Numerous publications attest to the advantage of this approach.

Nevertheless, the OMV approach also has some disadvantages. Thus, faced with the increased regulatory requirements, the characterization and quantification of the various components of OMVs, and more so the possibility of producing batches that are exactly the same, remain a tricky problem.

Other approaches have been developed in order to more readily control the content of a vaccine.

One of these alternative approaches consists in purifying LPS and in detoxifying it. Various detoxification methods are already known: chemical, genetic or enzymatic, or alternatively by complexation with a peptide or inclusion in liposomes. Once detoxified, the LPS can be conjugated to a carrier polypeptide or peptide.

With a view to producing a vaccine, the purified and detoxified LPS can be used alone or as a mixture, in particular with one or more proteins of vaccine interest, and more particularly with one or more outer membrane proteins. The proteins will have been obtained beforehand by recombinant process or in native form and then purified.

Although LPS is reputed to be immunogenic, the addition of an adjuvant—i.e. of a molecule capable of increasing the immune response of an organism against another molecule (in this case, LPS)—can prove to be very beneficial. It then remains to select, among all known adjuvants, the one that will function optimally with LPS.

In the vaccines field, one of the major stakes over the coming years will in particular be that of placing on the market a vaccine for preventing all *Neisseria meningitidis* infections. *N. meningitidis* is responsible for a certain number of pathologies, among which the dominant ones are meningitis and meningococcemia, but also arthritis and pericarditis. Meningococcemia can be complicated by *purpura fulminans* and by fatal septic shock.

In general, meningitis is either of viral origin or of bacterial origin. In developed countries, the bacteria mainly responsible are: *N. meningitidis* and *Streptococcus pneumoniae*, which are respectively involved in approximately 40 and 50% of cases of bacterial meningitis. In developing countries, *Haemophilus influenzae* also remains an important source of meningitis.

In France, there are approximately 600 to 800 cases per year of meningitis caused by *N. meningitidis*. In the United States, the number of cases comes to approximately 2500 to 3000 per year.

The *N. meningitidis* species is subdivided into serogroups depending on the nature of the capsular polysaccharides. Although about twelve serogroups exist, 90% of meningitis cases can be attributed to the serogroups: A, B, C, Y and W135.

Effective capsular polysaccharide-based vaccines exist for preventing meningitis caused by *N. meningitidis* serogroups A, C, Y and W135. These polysaccharides as such are only slightly immunogenic or are not immunogenic in children under 2 years old and do not induce any immune memory. However, these drawbacks can be overcome by conjugating these polysaccharides to a carrier protein.

On the other hand, the polysaccharide from *N. meningitidis* group B is barely immunogenic or not immunogenic in humans, whether it is in conjugated or nonconjugated form (Bruge et al, Vaccine (2004) 22: 1087). Thus, it appears to be highly desirable to seek a vaccine against meningitis induced by *N. meningitidis*, in particular of serogroup B, other than a capsular polysaccharide-based vaccine.

To this end, various *N. meningitidis* outer membrane proteins have already been proposed as a vaccine antigen, along with LPS. Quite a large number of *N. meningitidis* proteins have already been the subject of investigative studies. Mention is in particular made of the human transferrin receptor which is composed of two subunits, TbpA and TbpB.

It has now been demonstrated, in mouse and rabbit models, that the immune response against lipopolysaccharide (LPS) can be improved when LPS is administered with the lipidated form of human-transferrin-binding protein subunit B (TbpB) from N. meningitidis, strain M982, produced recombinantly. This has been observed using various forms of LPS. To observe this effect, it is sufficient for the LPS and the TbpB to be brought together, in whatever form, i.a. simple mixture, proteoliposomes or alternatively conjugated. To attempt to explain the results, it is postulated that the adjuvant effect of the TbpB on the LPS is, at least in part, due to the association, in the same molecule, of a fatty acid chain which plays in particular the role of a Toll-like receptor 2 (TLR2) agonist and of T-helper epitopes.

In other words, the results generated, as reported in the experimental section of the present patent application, teaches that the TbpB lipoprotein is capable of adjuvanting LPS.

This is the reason why the invention relates to a method for adjuvanting LPS, according to which:

(i) LPS or LPS liposomes (LPS formulated in liposomes) is (are) mixed with the lipidated human-transferrin receptor subunit B (lipidated TbpB) of *Neisseria meningitidis* or a lipidated fragment thereof;

(ii) LPS and the lipidated TbpB of *N. meningitidis* or a lipidated fragment thereof are formulated together in liposomes; or (iii) LPS is conjugated with the lipidated TbpB of *N. meningitidis* or a lipidated fragment thereof;

in order to obtain a preparation which does not contain OMVs and which is capable of inducing, after administration to a mammal, an anti-LPS immune response which is improved by comparison with the anti-LPS immune response observed after administration of the corresponding preparation in which the lipidated TbpB of *N. meningitidis* or a lipidated fragment thereof is omitted.

It is readily understood that the preparation thus obtained also does not contain proteosomes (undefined mixture of membrane proteins) directly prepared from their natural bacterial origin. Thus, porins such as PorA and PorB, which are major outer membrane proteins of Gram-negative bacteria, are absent, i.a. in their nonrecombinant form, preferably definitively absent in whatever form, from a preparation obtained by means of the method according to the invention.

In other words, the invention relates to the use as adjuvant of the lipidated human-transferrin receptor subunit B (lipidated TbpB) of *Neisseria meningitidis* or a lipidated fragment thereof, in order to improve the immune response of a mammal against an LPS from a Gram-negative bacterium by comparison with the anti-LPS immune response observed in the absence of the lipidated human-transferrin receptor subunit B (lipidated TbpB) of *Neisseria meningitidis* or a lipidated fragment thereof.

In the following part of the description, the term "or a lipidated fragment thereof" no longer appears for simplicity' sake. However, this term remains under-stated each time the term "lipidated TbpB" or "TbpB" is written down.

The objective that the present invention aims to accomplish—i.e. the adjuvantation of LPS—is materialized by an improved anti-LPS immune response. This improvement can be noted in one or more sphere(s) of the specific immune response, in particular in the sphere of the humoral response, also known as antibody response, and/or in the sphere of the cell-mediated response.

It may involve an increased production of one or more type(s) or subtype(s) of antibodies, IgA, IgM and IgG including the IgG subclasses capable of fixing complement.

It may also involve reinforcing a desired property, for example the bactericidal nature of the antibodies, which can be conveniently assessed against the strain of origin of the LPS (homologous strain). According to an advantageous aspect, the bactericidal nature of the antibodies will also be exerted against at least one heterologous strain.

Typically, the analysis of the antibody response and also the evaluation of the bactericidal nature can be carried out following one or more administration(s) of the preparation obtained by means of the method according to the invention; advantageously, after two or three consecutive administrations separated over time. According to one advantageous embodiment, a blood sample is taken not long before the first administration (for example, 1 to 7 days before), and then one or more administrations are carried out, 2 to 8 weeks apart, depending on the recipient mammal. A blood sample is taken 2 to 4 weeks after the final administration.

In the presence of lipidated TbpB, the anti-LPS IgA, IgM or IgG antibody response, as can be measured, for example in ELISA units, is increased after the final administration, e.g. the second or third administration, at least by a factor of 1.2, 1.4 or 1.6; preferably, by at least a factor of 1.8, 2, 2.2, 2.4, 2.6, 2.8, 3 or more.

Several known methods exist for assessing and expressing the bactericidal activity; one of them is described in the experimental section.

In general, a test preparation is administered to individuals, for example animals, one or more times with a certain amount of time in-between. Samples of the sera of the individuals are taken; then the bactericidal activity thereof is measured.

According to the method described in the experimental section, the bactericidal titer of a serum is expressed as being the inverse of the serum dilution that gives 50% bacterial death by comparison with the "complement" control. Then, the geometric mean titer (GMT) of the sera from which the sample is taken at an identical time from the same group of individuals—i.e. of individuals having all received the same product, is calculated. Finally, for each individual, the seroconversion rate is conventionally established as being, e.g., the ratio bactericidal titer at time T after administration:bactericidal titer before administration. For each group of individuals, the seroconversion rate which characterizes it, is conventionally established as being the ratio GMT at time T after administration:GMT before administration. Thus, the seroconversion rate measures the increase in the bactericidal titer. Alternatively, the seroconversion rate may also be expressed in "fold increase" as being the ratio GMT of sera of the animals immunized with the antigen:GMT of the sera of the animals immunized with the negative control.

The bactericidal activity is tested against a strain of the same immunotype as the LPS of the test preparation. This bactericidal activity is considered as being satisfactory if, after the final administration:

(i) the percentage of individuals having received the test preparation and exhibiting an increase in the bactericidal titer by at least a factor of 3, preferably 4 (compared with that measured before any administration), is greater than 60%, advantageously greater than 70%, preferably greater than 80% of the total individuals tested, particularly preferably equal to 100% of the total individuals tested; or, preferably and, (ii) the seroconversion rate characterizing a group of individuals having received the test preparation is greater than or equal to 4, advantageously greater than or equal to 8 or 10, preferably greater than or equal to 50 or 68, particularly preferably greater than or equal to 75 or 138.

LPS

The LPS that can be adjuvanted by means of the method according to the invention may be any LPS from Gram-negative bacteria, whether they are enteric or nonenteric, preferably pathogenic. According to one particular aspect, it may be LPS from nonenteric bacteria of genera such as *Neisseriae, Bordetellae, Branhamellas, Haemophilus* and *Moraxellae*. The LPS from these bacteria is also referred to as LOS (lipooligosaccharide) owing to the absence of O-specific polysaccharide. By way of additional example, mention is made of LPS/LOS from the genera or species *Klebsiella, Pseudomonas, Burkolderia, Porphyromonas, Franciscella, Yersinia, Enterobacter, Salmonella, Shigella* or *E. coli*; and most particularly the LOS from *N. meningitidis*.

*N. meningitidis* strains are classified in several immunotypes (IT L1 to IT L13), as a function of their reactivity with a series of antibodies that recognize various LOS epitopes (Achtman et al, 1992, J. Infect. Dis. 165: 53-68). As a direct consequence of this, the LOS from these *N. meningitidis* strains may also be referred to LOS of immunotype L1 to L13. The differences between immunotypes originate from variations in the composition and in the conformation of the oligosaccharide chains. This is shown in the table below, derived from Table 2 of Braun et al, Vaccine (2004) 22: 898, supplemented with data obtained subsequently and relating to immunotypes L9 (Schoudhury et al, Carbohydr. Res. (2008) 343: 2771) and L11 (Mistretta et al, (2008) Poster at the 16th International Pathogenic Neisseria Conference, Rotterdam):

The Galβ1-4GlcNAcβ1-3Galβ1-4Glcβ1-4 carbohydrate unit or lacto-N-neotetraose unit which is present in the α chain of certain *N. meningitidis* LPS immunotypes constitutes an epitope which can potentially crossreact with human erythrocytes. Thus, with a view to producing a vaccine for use in humans, it is advisable to choose an LPS which does not possess this unit. It may therefore be particularly advantageous to use an LOS of a *N. meningitidis* strain immunotype L8 (hereinafter called LOS of immunotype L8), in particular of strain A1 of *N. meningitidis* (Zhu, Klutch & Tsai, FEMS Microbiology Letters (2001) 203:173 as well as Gu, Tsai & Karpas, J. Clin. Microbiol. (August 1992) 30 (8): 2047) which is publicly available among the scientific community.

Alternatively, it is also possible to envisage starting, for example, with a strain of immunotype L2 or L3 in which a gene involved in the biosynthesis of the α chain has been inactivated by mutation, so as to obtain an incomplete LNnT structure. Such mutations are proposed in patent application WO 04/014417. This involves extinguishing, by mutation, the lgtB, lgtE (or lgtH), lgtA or lgtA and lgtC genes. Thus, it appears to be possible and advantageous to use an LPS originating from an *N. meningitidis* strain of immunotype L2 or L3 which is lgtB$^-$, lgtE$^-$ (or lgtH$^-$), lgtA$^-$ or lgtA$^-$ and lgtC$^-$.

For the purposes of the present invention, the LPS may be obtained by conventional means: in particular, it can be extracted from a bacterial culture, and then purified according to conventional methods. Many methods of production are

```
                            KDO
                            |α2-4
                   β1-4 α1-5|α2-6
         α chain  R-Glc-Hep-KDO-Lipid A
                        |α1-3
         β chain  R2-Hep-R3
                        |α1-2
                       GlcNAc γ chain
```

| IT  | α chain (including the R1 substituent)                        | R1           | R2             |
|-----|---------------------------------------------------------------|--------------|----------------|
| L1  | NeuNAcα2-6Galα1-4Galβ1-4Glcβ1-4                               | PEA-3        | —              |
| L2  | NeuNAcα2-3Galβ1-4GlcNAcβ1-3Galβ1-4 Glcβ1-4                    | Glcα (1-3)** | PEA-6 or PEA-7 |
| L3  | NeuNAcα2-3Galβ1-4GlcNAcβ1-3Galβ1-4 Glcβ1-4                    | PEA-3        | —              |
| L4  | NeuNAcα2-3Galβ1-4GlcNAcβ1-3Galβ1-4 Glcβ1-4                    | —            | PEA-6          |
| L5  | NeuNAcα2-3Galβ1-4GlcNAcβ1-3Galβ1-4Glcβ1-4Glcα (1-3)           | —            | —              |
| L6  | GlcNAcβ1-3Galβ1-4 Glcβ1-4                                     | —            | PEA-6 or PEA-7 |
| L7  | Galβ1-4GlcNAcβ1-3Galβ1-4 Glcβ1-4                              | PEA-3        | —              |
| L8  | Galβ1-4 Glcβ1-4                                               | PEA-3        | —              |
| L9  | Galβ1-4GlcNAcβ1-3Galβ1-4 Glcβ1-4                              | —            | PEA-6          |
| L10 | n.d.                                                          | n.d.         | n.d.           |
| L11 | Glcβ1-4Glcβ1-4                                                | PEA-3        | PEA-6          |
| L12 | n.d                                                           | n.d.         | n.d.           |
| L13 | n.d                                                           | n.d.         | n.d.           | n.d.: not determined.
**When R2 is a glucose residue, R2 is commonly called β chain.

It may be noted, inter alia, that certain LOSs may be sialylated (presence of N-acetylneuraminic acid on the terminal galactose residue (Gal) of the α chain). Thus, immunotypes L3 and L7 differ only by the respective presence/absence of this sialylation. Moreover, most LOSs are substituted with an O-acetyl group on the glucosamine residue (α-GlcNAc or γ chain) of the inner core (Wakarchuk et al. (1998) Eur. J. Biochem. 254: 626; Gamian et al. (1992) J. Biol. Chem. 267: 922; Kogan et al (1997) Carbohydr. Res. 298: 191; Di Fabio et al. (1990) Can. J. Chem. 68: 1029; Michon et al. (1990) J. Biol. Chem. 275: 9716; Choudhury et al. (above); and Mistretta et al. (above)).

described in the literature. By way of example, mention is made, i.a., of Westphal & Jann, (1965) Meth. Carbohydr. Chem. 5: 83; Gu & Tsaï, 1993, Infect. Immun. 61 (5): 1873; Wu et al, 1987, Anal. Biochem. 160: 281 and U.S. Pat. No. 6,531,131. An LPS preparation can be quantified according to well-known procedures. Assaying of KDO by high performance anion exchange chromatography (HPAEC-PAD) is a method which is most particularly suitable.

The TbpB of *N. Meningitidis*

The TbpB of *N. meningitidis* as naturally produced by *N. meningitidis* is a lipoprotein. Nevertheless, it can also be recombinantly produced in an expression system which in particular makes it possible to lipidate the polypeptide in the very organism responsible for the expression. According to one preferred embodiment, the lipidated TbpB is a recombinant lipidated TbpB—i.e. recombinantly produced, e.g. in a heterologous expression system.

An expression system typically uses an expression cassette and a prokaryotic or eukaryotic (yeast) host cell. The expression cassette encodes a TbpB precursor (also called pro-TbpB). This precursor is constituted of a signal sequence characteristic of a lipoprotein and of the sequence of the mature protein having a cysteine residue in the N-terminal position. The three amino acids in the C-terminal position of the signal sequence and also the cysteine residue in the N-terminal position of the mature sequence constitute the cleavage site (also called lipobox). This lipobox typically has the sequence: Leu-Ser/Ala-Ala/Gly-Cys (SEQ ID NO: 1). A typical signal sequence is that of the E. coli lipoprotein Lpp: Met-Lys-Ala-Thr-Lys-Leu-Val-Leu-Gly-Ala-Val-Ile-Leu-Gly-Ser-Thr-Leu-Leu-Ala-Gly (SEQ ID NO: 2). Thus, in the expression cassette, the polynucleotide sequence encoding the amino acid sequence of TbpB is fused, in the 5' position, to an appropriate signal sequence.

According to a particularly preferred embodiment, the LPS and the lipidated TbpB both originate from the same bacterial species, namely N. meningitidis.

A bacterial lipoprotein is, like any protein, defined by an amino acid sequence. Within a genus or a species, this amino acid sequence may display a certain degree of variability without this affecting the biological function of the lipoprotein. This is then referred to as an "allelic variant". There are a multiplicity of sequences having a certain degree of identity between them that correspond to a TbpB of a specific strain, each of the sequences originating from a particular strain, one being the allelic variant of the other.

Thus, it will be easily understood that the present invention is not limited to the use of a TbpB defined by a particular amino acid sequence. Any reference to an amino acid sequence is made by way of non-limiting illustration.

The present invention is also not limited to a wild-type lipidated TbpB. In fact, it may not only be a wild-type form, but also a form mutated by addition, substitution or deletion of one or more amino acids.

For use in the present invention, the lipidated TbpB fragment, and more particularly the "polypeptide" moiety of the fragment, comprises one or more T-helper epitope(s)—i.e. epitopes capable of being recognized by T-helper cells—and of activating them. Advantageously, they are T-helper epitopes characteristic of the organism for which the LPS-based vaccine is intended (a mammal, in particular a human)—i.e. epitopes capable of being recognized by the T-helper cells of the recipient organism and of activating them.

The open reading frame (ORF) encoding the TbpB (tbpB) of several strains of N. meningitidis has already been identified by its sequence, and the amino acid sequence of the corresponding protein has been deduced. Thus, the tbpB and TbpB sequences of the N. meningitidis strains serotype B strains, M982 and B16B6, are disclosed in patent application EP 586 266. Those of the meningococcal strains MC58 (serogroup B), Z2491 (serogroup A) and FAM18 (serogroup C) are respectively disclosed in Tettelin et al, Science, March 2000, 287: 1809 or WO 00/66791; Parkhill et al, Nature (March 2000) 404: 502; and Bentley et al, PLoS Genet., 3, e23 (2007).

Since the identification of the latter sequences was carried out in the context of complete genome sequencing, they were assigned an accession number. Thus, in Tettelin et al (above) or WO 00/66791, the tbpB/TbpB sequences of the MC58 strain are denoted under the reference NMB 0460. In the remaining text, the N. meningitidis proteins may be denoted without this making reference in a limiting manner to the sequences of the MC58 strain.

Two major TbpB families have to date been documented in N. meningitidis: isotype I characterized by a tbpB gene of 1.8 kb, and isotype II characterized by a tbpB gene of 2.1 kb. Isotype I is expressed in the ST-11 clonal complex, and isotype II is expressed in the ST-8, ST-18, ST-32 and ST-41/44 clonal complexes (Harrison et al, BMC Microbiol. 2008, 8: 66). The B16B6 (serogroup B) and FAM18 (serogroup C) strains are representatives of isotype I; the M982, BZ83 and 8680 strains are representatives of isotype II. For the purposes of the invention, the TbpBs of the two isotypes can be used without distinction.

According to a first embodiment of the method of the invention, LPS is mixed with the lipidated TbpB. The LPS may be (i) simply purified, (ii) in conjugated form—i.e. covalently bonded to a carrier polypeptide, or else (iii) formulated in liposomes.

The LPS may be obtained in purified form by conventional means; in particular, it may be extracted from a culture of Gram-negative bacteria and then purified according to conventional techniques, as described, for example, in Gu & Tsaï, 1993, Infect. Immun. 61 (5): 1873, Wu et al, 1987, Anal. Biochem. 160: 281 and U.S. Pat. No. 6,531,131. An LPS preparation can also be quantified by using known techniques. A practical method consists in assaying the KDO by HPAEC-PAD (high performance anion exchange chromatography).

PS Conjugate

When the lipidated TbpB is mixed with a conjugated LPS, the LPS may be conjugated to any oligopeptide or any carrier protein in use in the vaccines field; and in particular pertussis, diphtheria or tetanus toxoid, the diphtheria toxin mutant named CRM197, a bacterial OMP (for example, N. meningitidis OMPC (outer-membrane protein C)), Pseudomonas exotoxin A, Haemophilus influenzae lipoprotein D, Streptococcus pneumoniae pneumolysin and Bordetella pertussis filamentous hemagglutinin.

Many conjugation methods exist in the technical field. Some are listed, for example, in patent applications EP 941 738 and WO 98/31393. Advantageous modes of conjugation are described in a subsequent section relating to LPS-lipidated TbpB conjugates. These modes of conjugation are likewise of use with a view to obtaining the conjugates envisioned in the present section.

Detoxification of the LPS

When the LPS is simply purified or in conjugated form, it is advisable to substantially detoxify it before mixing (or before conjugation and then mixing). The toxicity of the LPS is due to its lipid A. However, it is not imperative to remove the lipid A in its entirety. In fact, since the toxicity is more particularly linked to a supramolecular conformation conferred by all the fatty acid chains borne by the disaccharide nucleus of the lipid, according to one advantageous embodiment, it is sufficient to act on these chains.

The detoxification can be obtained according to various approaches: chemical, enzymatic or genetic or alternatively by complexation with a peptide analog of polymyxin B.

The chemical approach consists in treating the LPS with a chemical agent. According to one particular embodiment, the LPS is subjected to mild acid hydrolysis with acetic acid which removes the lipid A and also the branched KDO(s) when it (they) is (are) present in the LPS structure. Such a treatment is, for example, described in Gu & Tsai Infect. Immun. (1993) 61: 1873. According to an alternative and preferred embodiment, the LPS is subjected to a de-O-acylation, preferably a primary de-O-acylation, i.a. by treatment with hydrazine, which hydrolyzes the esterified primary fatty acid chains of the lipid A. Such a treatment is, for example, described in U.S. Pat. No. 6,531,131, Gupta et al, Infect. Immun. (1992) 60 (8): 3201 and Gu et al, Infect. Immun. (1996) 64 (10): 4047.

The enzymatic approach consists in placing the LPS in the presence of lipases capable of digesting the esterified fatty acid chains of the lipid A. Such lipases are produced by the amoeba *Dictyostelium discoideum*. According to one particularly advantageous embodiment, the amoeba and a Gram-negative bacterium that can be phagocytosed by the amoeba, such as *N. meningitidis*, are cultured together (coculture). The supernatant is then recovered and the LPS is extracted from the supernatant which is then free of fatty acid chains. It may also be an acyloxyacyl hydrolase produced by certain human cells (patent WO 87/07297 Munford R.) or by *Salmonella typhimurium* (Trent et al 2001 J. Biol. Chem. 276: 9083-9092; Reynolds et al. 2006 J. Biol. Chem. 281: 21974-21987) (enzyme encoded by the PagL or LpxR genes in the latter case).

The genetic approach consists in using an LPS produced by a bacterial strain of which the genotype is such that the entity of the LPS normally responsible for its toxicity (lipid A, and more particularly the lipid tails of lipid A) has a greatly reduced or even nonexistent degree of toxicity. Such a bacterial strain can be conveniently obtained by mutation. Starting from a wild-type strain (i.e. a strain producing a toxic LPS), this then involves inactivating, by mutation, certain genes involved in the biosynthesis of the fatty acid chains, or in the attachment thereof to the disaccharide nucleus of lipid A. Thus, it is possible to envision inactivating the lpxL1 or lpxL2 genes (also called htrB1/htrB2) of *N. meningitidis* or equivalents thereof in other species (for example, the equivalents of the meningiocal lpxL1 and lpxL2 genes are respectively called msbB or lpxM and htrB or lpxL in *E. coli*.). A mutation that inactivates one of these genes results in an LPS devoid of one or of two secondary acyl chains. lpxL1 or L2 mutants of *N. meningitidis* or of *Haemophilus influenzae* are in particular described in patent applications WO 00/26384, US 2004/0171133 and WO 97/019688. In *N. meningitidis*, the endogenous lpxA gene can also be replaced with the homologous gene originating from *E. coli* or *Pseudomonas aeruginosa*. The fatty acid chains thereof are modified, resulting in a less toxic lipid A (Steeghs et al, Cell. Microbiol. (2002) 4 (9): 599).

Finally, a fourth approach consists in complexing the LPS with a peptide analog of polymyxin B, as is, for example, described in patent application WO 06/108586. The LPS that is complexed and consequently detoxified is called endotoxoid.

LPS in Liposomes

When the LPS is formulated in liposomes, detoxification is not necessarily required beforehand. This is because LPS in liposomes—i.e. associated with the lipid bilayer forming the liposomes—may experience a very substantial decrease in toxicity. The size of this decrease, which can be as much as a substantial loss, depends partly on the nature of the components forming the liposome. Thus, when positively charged components (components of cationic nature) are used, the loss of toxicity may be greater than with uncharged (neutral) or anionic components.

The term "liposomes" is intended to mean a synthetic entity, preferably a synthetic vesicle, formed of at least one lipid bilayer membrane (or matrix) enclosing an aqueous compartment. For the purposes of the present invention, the liposomes may be unilamellar (a single bilayer membrane) or multilamellar (several membranes layered like an onion). The lipids constituting the bilayer membrane comprise a nonpolar region which, typically, is made of chain(s) of fatty acids or of cholesterol, and a polar region, typically made of a phosphate group and/or of tertiary or quaternary ammonium salts. Depending on its composition, the polar region may, in particular at physiological pH (pH≈7) carry either a negative (anionic lipid) or positive (cationic lipid) net (overall) surface charge, or not carry a net charge (neutral lipid).

For the purposes of the present invention, the liposomes may be liposomes of any type; in particular, they may be constituted of any lipid known to be of use in the production of liposomes. The lipid(s) that go(es) to make up the composition of the liposomes may be neutral, anionic or cationic lipid(s); the latter being preferred. These lipids may be of natural origin (plant or egg extraction products, for example) or synthetic origin; the latter being preferred. The liposomes may also be constituted of a mixture of these lipids; for example, of a cationic or anionic lipid and of a neutral lipid, as a mixture. In the latter two cases, the neutral lipid is often referred to as colipid. According to one advantageous embodiment, the charged (cationic or anionic) lipid: neutral lipid molar ratio is between 10:1 and 1:10, advantageously between 4:1 and 1:4, preferably between 3:1 and 1:3, limits included.

With regard to the neutral lipids, mention is made, by way of example, of: (i) cholesterol; (ii) phosphatidylcholines such as, for example, 1,2-diacyl-sn-glycero-3-phosphocholines, e.g. 1,2-dioleoyl-sn-glycero-3-phosphocholine (DOPC), and also 1-acyl-2-acyl-sn-glycero-3-phosphocholines of which the acyl chains are different than one another (mixed acyl chains); and (iii) phosphatidylethanolamines such as, for example, 1,2-diacyl-sn-glycero-3-phosphoethanolamines, e.g. 1,2-dioleoyl-sn-glycero-3-phosphoethanolamine (DOPE), and also 1-acyl-2-acyl-sn-glycero-3-phosphoethanolamines bearing mixed acyl chains.

With regard to the anionic lipids, mention is made, by way of example, of: (i) cholesteryl hemisuccinate (CHEMS); (ii) phosphatidylserines such as 1,2-diacyl-sn-glycero-3-[phospho-L-serine]s, e.g. 1,2-dioleoyl-sn-glycero-3-[phospho-L-serine] (DOPS), and 1-acyl-2-acyl-sn-glycero-3-[phospho-L-serine]s bearing mixed acyl chains; (iii) phosphatidylglycerols such as 1,2-diacyl-sn-glycero-3-[phospho-rac-(1-glycerol)]s, e.g. 1,2-dioleoyl-sn-glycero-3-[phospho-rac-(1-glycerol)] (DOPG), and 1-acyl-2-acyl-sn-glycero-3-[phospho-rac-(1-glycerol)]s bearing mixed acyl chains; (iv) phosphatidic acids such as 1,2-diacyl-sn-glycero-3-phosphates, e.g. 1,2-dioleoyl-sn-glycero-3-phosphate (DOPA), and 1-acyl-2-acyl-sn-glycero-3-phosphates bearing mixed acyl chains; and (v) phosphatidylinositols such as 1,2-diacyl-sn-glycero-3-(phosphoinositol)s, e.g. 1,2-dioleoyl-sn-glycero-3-(phosphoinositol) (DOPI), and 1-acyl-2-acyl-sn-glycero-3-(phosphoinositol)s bearing mixed acyl chains.

With regard to the cationic lipids, mention is made, by way of example, of:

(i) lipophilic amines or alkylamines such as, for example, dimethyldioctadecylammonium (DDA), trimethyldioctadecylammonium (DTA) or structural homologs of DDA and of DTA [these alkylamines are advantageously used in the form of a salt; mention is made, for example, of dimethyldioctadecylammonium bromide (DDAB)];

(ii) octadecenoyloxy(ethyl-2-heptadecenyl-3-hydroxyethyl) imidazolinium (DOTIM) and structural homologs thereof;

(iii) lipospermines such as N-palmitoyl-D-erythrosphingosyl-1-O-carbamoylspermine (CCS) and dioctadecylamidoglycylspermine (DOGS, transfectam);

(iv) lipids incorporating an ethylphosphocholine structure, such as cationic derivatives of phospholipids, in particular phosphoric ester derivatives of phosphatidylcholine, for example those described in patent application WO 05/049080 and including, in particular:

1,2-dimyristoyl-sn-glycero-3-ethylphosphocholine,
1,2-dipalmitoyl-sn-glycero-3-ethylphosphocholine,
1,2-palmitoyloleoyl-sn-glycero-3-ethylphosphocholine,
1,2-distearoyl-sn-glycero-3-ethylphosphocholine (DSPC),
1,2-dioleyl-sn-glycero-3-ethylphosphocholine (DOEPC or EDOPC or ethyl-DOPC or ethyl PC),
and also structural homologs thereof;

(v) lipids incorporating a trimethylammonium structure, such as N-(1-[2,3-dioleyloxy]propyl)-N,N,N-trimethylammonium (DOTMA) and structural homologs thereof and those incorporating a trimethylammonium propane structure, such as 1,2-dioleyl-3-trimethylammonium propane (DOTAP) and structural homologs thereof; and also lipids incorporating a dimethylammonium structure, such as 1,2-dioleyl-3-dimethylammonium propane (DODAP) and structural homologs thereof; and (vi) cationic derivatives of cholesterol, such as 3β-[N—(N', N'-dimethylaminoethane)-carbamoyl]cholesterol (DC-Chol) or other cationic derivatives of cholesterol, such as those described in U.S. Pat. No. 5,283,185, and in particular cholesteryl-3β-carboxamidoethylenetrimethylammonium iodide, cholesteryl-3β-carboxyamidoethylene-amine, cholesteryl-3β-oxysuccinamidoethylenetrimethylammonium iodide and 3β-[N-(polyethyleneimine)carbamoyl]cholesterol.

The term "structural homologs" signifies lipids which have the characteristic structure of the reference lipid while at the same time differing therefrom by virtue of secondary modifications, especially in the nonpolar region, in particular of the number of carbon atoms and of double bonds in the fatty acid chains.

These fatty acids, which are also found in the neutral and anionic phospholipids, are, for example, dodecanoic or lauric acid (C12:0), tetradecanoic or myristic acid (C14:0), hexadecanoic or palmitic acid (C16:0), cis-9-hexadecanoic or palmitoleic acid (C16:1), octadecanoic or stearic acid (C18:0), cis-9-octadecanoic or oleic acid (C18:1), cis,cis-9,12-octadecadienoic or linoleic acid (C18:2), cis-cis-6,9-octadecadienoic acid (C18:2), all-cis-9,12,15-octadecatrienoic or α-linolenic acid (C18:3), all-cis-6,9,12-octadecatrienoic or γ-linolenic acid (C18:3), eicosanoic or arachidic acid (C20:0), cis-9-eicosenoic or gadoleic acid (C20:1), all-cis-8,11,14-eicosatrienoic acid (C20:3), all-cis-5,8,11,14-eicosatetraenoic or arachidonic acid (C20:4), all-cis-5,8,11,14,17-eicosapentaneoic acid (C20:5), docosanoic or behenic acid (C22:0), all-cis-7,10,13,16,19-docosapentaenoic acid (C22:5), all-cis-4,7,10,13,16,19-docosahexaenoic acid (C22:6) and tetracosanoic or lignoceric acid (C24:0).

The characteristic structure of DDAB is:

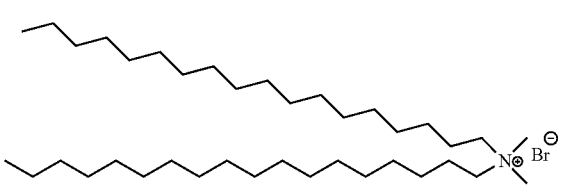 [SMILES: CCCCCCCCCCCCCCCCCC[N+](C)(C)CCCCCCCCCCCCCCCCCC ; [Br-]]

The characteristic structure of EDOPC is:

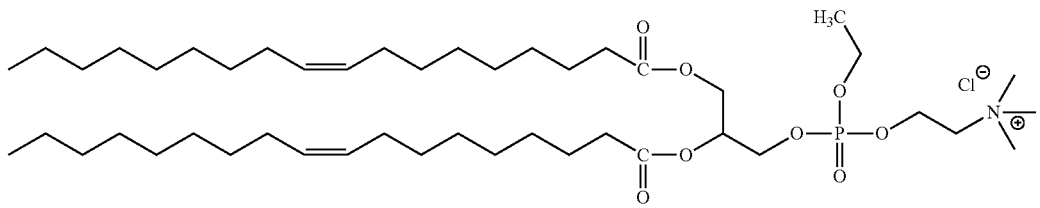 [SMILES: CCCCCCCC/C=C\CCCCCCCC(=O)OCC(COP(=O)(OCC)OCC[N+](C)(C)C)OC(=O)CCCCCCC/C=C\CCCCCCCC ; [Cl-]]

The characteristic structure of DOTAP is:

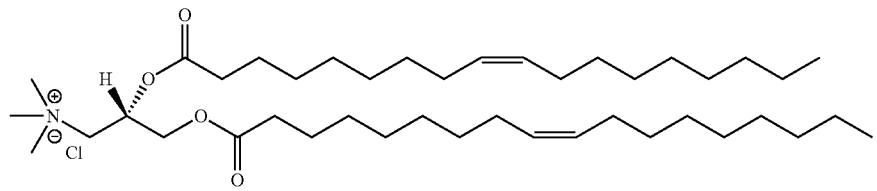

The characteristic structure of DC-chol is:

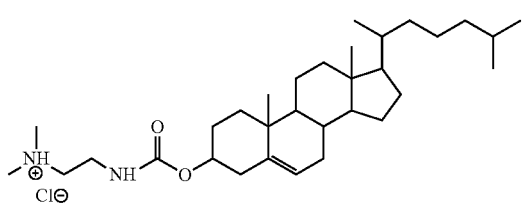 [SMILES: CC(C)CCCC(C)C1CCC2C3CC=C4CC(OC(=O)NCC[NH+](C)C)CCC4(C)C3CCC12C ; [Cl-]]

According to one particular embodiment, a mixture of cationic lipid and neutral lipid is used. By way of example, mention is made of:

a mixture of DC-chol and DOPE, in particular in a DC-chol:DOPE molar ratio ranging from 10:1 to 1:10, advantageously from 4:1 to 1:4, preferably from approximately 3:1 to 1:3;

a mixture of EDOPC and cholesterol, in particular in an EDOPC:cholesterol molar ratio ranging from 10:1 to 1:10, advantageously from 4:1 to 1:4, preferably from approximately 3:1 to 1:3; and a mixture of E-DOPC and DOPE, in particular in an EDOPC:DOPE molar ratio ranging from 10:1 to 1:10, advantageously from 4:1 to 1:4, preferably from approximately 3:1 to 1:3.

According to one advantageous method of preparation, in an initial step, a dry lipid film is prepared with all the compounds that go to make up the composition of the liposomes. The lipid film is then reconstituted in an aqueous medium, in the presence of LPS, for example in a lipid:LPS molar ratio of 100 to 500, advantageously of 100 to 400, preferably of 200 to 300, most particularly preferably of approximately 250. In general, it is considered that this same molar ratio should not substantially vary at the end of the method of preparing the LPS liposomes.

In a general manner, the reconstitution step in an aqueous medium results in the spontaneous formation of multilamellar vesicles, the size of which is subsequently homogenized by gradually decreasing the number of lamellae by extrusion, for example using an extruder, by passing the lipid suspension, under a nitrogen pressure, through polycarbonate membranes with decreasing pore diameters (0.8, 0.4, 0.2 µm). The extrusion process can also be replaced with another process using a detergent (surfactant) which disperses lipids. This detergent is subsequently removed by dialysis or by adsorption onto porous polystyrene microbeads with a particular affinity for detergent (BioBeads). When the surfactant is removed from the lipid dispersion, the lipids reorganize in a double layer.

At the end of the incorporation of the LPS into liposomes, a mixture constituted of ad hoc liposomes and of LPS in free form may commonly be obtained. Advantageously, the liposomes are then purified in order to be rid of the LPS in free form.

The LPS or the LPS liposomes are finally mixed with the lipidated TbpB in an LPS: lipidated TbpB molar ratio of from $10^{-2}$ to $10^3$, advantageously from $10^{-1}$ to $10^2$, preferably from 1 to 50, most particularly preferably from 15 to 30, or of approximately 20.

By way of example, when LPS from N. meningitidis immunotype L8 and lipidated TbpB from N. meningitidis are used, the molar ratio may typically be approximately 20 or 25, depending on whether the TbpB isotype is I or II. When LPS from N. meningitidis immunotype L6 and lipidated TbpB from N. meningitidis are used, the molar ratio may typically be approximately 19 or 23, depending on whether the TbpB isotype is I or II.

The lipidated TbpB that is used to prepare this mixture may be simply purified or alternatively be incorporated in liposomes; the first embodiment being, however, preferred.

The purified lipidated TbpB, owing to its lipid tail, is expected to exhibit a certain degree of insolubility under purely aqueous conditions. Consequently, it should be placed under conditions that favour its solubility. Those skilled in the art have a good grasp of the techniques aimed at making a purified lipoprotein soluble. It is, for example, possible to use a detergent during the purification of the lipoprotein, in order to obtain a preparation of a purified lipoprotein that is soluble in the presence of detergent. The amount of detergent remaining in the final preparation will be controlled in such a way that it is just sufficient to maintain the purified lipoprotein in soluble form. Alternatively, it is possible to completely remove the detergent used during the purification, and then to add another product which also has the ability to maintain the purified lipoprotein in soluble form.

According to a second embodiment of the method of the invention, the LPS and the lipidated TbpB are formulated together in liposomes (proteoliposomes). The liposomes used for this purpose are the same as those previously described for the formulation inliposomes of LPS alone. One means for carrying this formulation through to a successful conclusion consists in formulating the LPS and the lipidated TbpB together in liposomes, for example by reconstituting a lipid film in an aqueous medium in the presence of LPS and of lipidated TbpB, in particular in:

a lipid:LPS molar ratio of from 100 to 500, advantageously from 100 to 400, preferably from 200 to 300, most particularly preferably of approximately 250; and/or an LPS: lipidated TbpB molar ratio of from $10^{-2}$ to $10^3$, advantageously from $10^{-1}$ to $10^2$, preferably from 1 to 50, most particularly preferably from 15 to 30, e.g. of approximately 20.

At the end of the incorporation of the LPS and the lipidated TbpB in liposomes, a mixture constituted of ad hoc liposomes (proteoliposomes), of LPS and/or lipidated TbpB in free form may commonly be obtained. Advantageously, the liposomes are then purified in order to be rid of the LPS in free form. Once the free LPS has been removed, the mixture can be used as it is for vaccine purposes, or else the liposomes can be further purified in order to be rid of the free lipidated TbpB. Once the liposomes have been completely purified, it is possible to envision adding back free lipidated TbpB, in particular in a defined amount.

According to one particular embodiment, the liposomes [LPS] or the proteoliposomes [LPS+lipidated TbpB] do not contain any polypeptide other than the lipidated TbpB acting as adjuvant for LPS. For example, it may be advantageous for the liposomes not to contain structural proteins of the outer membrane of Gram-negative bacteria, such as OMPs or porins, also not to contain any structural protein of the outer membrane of the bacterium from which the LPS was extracted.

In another particular embodiment, a mixture obtained according to the method which is the subject of the present application does not contain structural proteins of the outer membrane of Gram-negative bacteria, such as OMPs or porins, or does not contain structural proteins of the outer membrane of the bacterium from which the LPS was extracted.

The LPS-Lipidated TbpB Conjugates

In a third embodiment of the method of the invention, the LPS is conjugated with the lipidated TbpB. Advantageously, it is advisable to substantially detoxify LPS before conjugation. The detoxification can be successfully carried out as described above, chemically, enzymatically, genetically or by complexation.

Many methods of conjugation exist in the technical field. Some are listed, for example, in patent applications EP 941 738 and WO 98/31393.

In general, the reactive groups of the LPS involved in the conjugation are those of the inner core or of lipid A. It may involve, inter alia, the acid function of the KDO, or else an aldehyde generated subsequent to an appropriate treatment on the disaccharide of lipid A. For example, a phosphatase treatment generates an aldehyde on the structure of the second glucosamine of lipid A from N. meningitidis (Brade H. (2002) J. Endotoxin Res. 8 (4): 295 Mieszala et al, (2003) Carbohydrate Res. 338: 167 and Cox et al, (2005) Vaccine 23 (5): 5054).

Advantageously, the method of conjugation makes use (i) of a bifunctional linker or (ii) of a spacer and of a linker.

For example, in the first case, the LPS is activated with a bifunctional coupling agent (linker) of formula R1—A—R2, such that the R2 radical reacts with a reactive group of the KDO or of the lipid A in order to obtain an activated LPS; the activated LPS is then conjugated with the lipidated TbpB such that the R1 radical reacts with a functional group borne by the lipidated TbpB, in order to obtain a conjugate.

For example, in the second case, the LPS is derivatized with a spacer of formula R3—B—R4 such that the R3 radical reacts with a reactive group of the KDO or of the lipid A in order to obtain a derivatized LPS; the derivatized LPS is then activated with a bifunctional coupling agent (linker) of formula R1—A—R2 such that the R2 radical reacts with the R4 radical in order to obtain a derivatized and activated LPS; finally, the derivatized and activated LPS is conjugated with the lipidated TbpB such that the R1 radical reacts with a functional group borne by the lipidated TbpB in order to obtain a conjugate.

In the second case, the process can also be carried out in the following way: the lipoprotein is derivatized with a spacer of formula R3—B—R4 such that the R4 radical reacts with a bifunctional group borne by the lipidated TbpB; the LPS is activated with a bifunctional linker of formula R1—A—R2 such that the R2 radical reacts with a reactive group of the KDO or of the lipid A, in order to obtain an activated LPS; and then the activated LPS is conjugated with the derivatized lipidated TbpB such that the R1 radical of the activated LPS reacts with the R3 radical of the derivatized lipidated TbpB, in order to obtain a conjugate.

In the formula of the spacer, B may be a carbon chain, preferably carbonyl, alkyl or alkylene, for example C1 to C12. R3 and R4 may independently be a thiol or amine group or a residue bearing same, for example a hydrazide group, i.e. $NH_2$—NH—O—. Compounds that may be used as a spacer have, for example, the formula $NH_2$—B—$NH_2$, or preferably $NH_2$—B—SH and $NH_2$—B—S—S—B'—$NH_2$. By way of particular example, mention is made of, cysteamine, cysteine, diamines, e.g. diaminohexane, adipic acid dihydrazide (ADH), urea and cystamine.

In the formula of the linker, A may be an aromatic or preferably aliphatic chain which is substituted or unsubstituted and which advantageously contains from 1 to 12 carbon atoms, preferably 3 to 8 carbon atoms. For example, A may be a C2 to C8 alkylene, a phenylene, a C7 to C12 aralkylene, a C2 to C8 alkyl, a phenyl, a C7 to C12 aralkyl, a C6 alkanoyloxy or a benzylcarbonyloxy, which may be substituted or unsubstituted.

The R2 radical is the functional group of the linker which creates the link with the LPS or with the derivatized LPS. Thus, R2 is a functional group which can react with a carboxyl, hydroxyl, aldehyde or amine group. If the linker must react with a hydroxyl, carboxyl or aldehyde group, R2 is preferably an amine group or a residue carrying an amine group, for example a hydrazide group, i.e. $NH_2$—NH—CO—. If the linker must react with an amine group, R2 is preferably a carboxyl, succinimidyl (e.g. N-hydroxysuccinimidyl) or sulfosuccinimidyl (e.g. N-hydroxysulfosuccinimidyl) group.

Thus, compounds that can be used as a linker may be chosen from adipic acid dihydrazide (ADH); sulfosuccinimidyl 6-(3-[2-pyridyldithio]propionamido)hexanoate (Sulfo-LC-SPDP); succinimidyl 6-(3-[2-pyridyldithio]propionamido)hexanoate (LC-SPDP); N-succinimidyl-S-acetyl thioacetate (SATA); N-succinimidyl 3-(2-pyridyldithio)propionate (SPDP); succinimidyl acetylthiopropionate (SATP); succinimidyl-4-(N-maleimidomethyl)cyclohexane-1-carboxylate (SMCC); maleimidobenzoyl-N-hydroxysuccinimide ester (MBS); N-succinimidyl (4-iodoacetyl)aminobenzoate (SIAB); succinimidyl 4-(p-maleimidophenyl)butyrate (SMPB); bromoacetic acid-N-hydroxysuccinimide (BANS) ester; dithiobis(succinimidylpropionate) (DTSSP); H-(γ-maleimidobutyryloxy)succinimide ester (GMBS); succinimidyl-4-(N-maleimidomethyl)cyclohexane-1-carboxylate; N-succinimidyl-4-(4-maleimidophenyl)butyrate; N-[β-maleimidocaproic acid]hydrazide (BMCH); N-succinimidyl-4-maleimidobutyrate; and N-succinimidyl-3-maleimidobenzoate.

By way of example, it is proposed to use the acid function of the KDO in order to derivatize the LPS with ADH in the presence of a carbodiimide [e.g. 1-ethyl-3-(3-dimethylaminopropyl)carbodiimide hydrochloride (EDAC)]. The amine function thus introduced is then reacted with the carboxyl functions of the lipidated TbpB, in the presence of EDAC, after having protected the amine functions of the latter (Wu et al (2005) Vaccine 23: 5177) or having converted them to acid functions (succinylation of the protein; Pavliakova et al, Infect. Immun. (1999) 67 (10): 5526).

Alternatively, it is proposed to use the acid function of the KDO in order to derivatize the LPS with cysteamine or cysteine in the presence of EDAC. The thiol function thus introduced is then reacted with the maleimide function of a homobifunctional linker, such as bismaleimidohexane; or a heterobifunctional linker, such as GMBS. In the first case, the maleimide function thus introduced is then reacted with the thiol functions of the lipidated TbpB. In the second case, the succinimidyl function of the derivatized and activated LPS is reacted with the amine functions of the lipopolypeptide.

Depending on the method of conjugation selected, the LPS and the lipidated TbpB are conjugated to one another in an LPS: lipidated TbpB molar ratio of from $10^{-1}$ to $10^2$, advantageously from 1 to $10^2$, preferably from 1 to 50; most particularly preferably of approximately 20.

According to another aspect, the invention relates to a vaccine which does not contain OMVs and which comprises (i) a vaccine antigen which is the LPS from a Gram-negative bacterium, optionally formulated in liposomes, conjugated to a carrier polypeptide or in an endotoxoid form, and (ii) an adjuvant of the anti-LPS immune response, which is the lipidated human-transferrin receptor subunit B (TbpB protein) of N. meningitidis or a lipidated fragment thereof; the LPS being present in sufficient amount for the anti-LPS immune response induced by the vaccine to be capable of protecting an individual against a disease caused by the Gram-negative bacterium.

It is readily understood that the vaccine according to the invention also does not contain proteosomes (undefined mixture of membrane proteins) directly prepared from their natural bacterial origin. Thus, porins such as PorA and PorB, which are major outer membrane proteins of Gram-negative bacteria, are absent, i.a. in their nonrecombinant form, preferably definitively absent in any form whatsoever.

A vaccine according to the invention may be available in a variety of forms according to varied modes. Thus, a vaccine according to the invention may comprise:

A—(i) a vaccine antigen which is the LPS from a Gram-negative bacterium and (ii) an adjuvant of the anti-LPS immune response which is the lipidated TbpB of N. meningitidis; the LPS being formulated in liposomes;

B—(i) a vaccine antigen which is the LPS from a Gram-negative bacterium and (ii) an adjuvant of the anti-LPS immune response which is the lipidated TbpB of N. meningitidis; the LPS and the TbpB being formulated together in liposomes;

C—(i) a vaccine antigen which is the LPS from a Gram-negative bacterium and (ii) an adjuvant of the anti-LPS immune response which is the lipidated TbpB of *N. meningitidis* a lipopolypeptide; the LPS being in endotoxoid form (i.e. complexed with a peptide analog of polymyxin B);
D—(i) a vaccine antigen which is the LPS from a Gram-negative bacterium and (ii) an adjuvant of the anti-LPS immune response which is the lipidated TbpB of *N. meningitidis*; the LPS being conjugated to a carrier polypeptide; or
E—(i) a vaccine antigen which is the LPS from a Gram-negative bacterium and (ii) an adjuvant of the anti-LPS immune response which is the TbpB of *N. meningitidis*; the LPS being conjugated to the TbpB.

A vaccine composition according to the invention is in particular of use for treating or preventing an infection with a Gram-negative bacterium which is a non-enteric bacterium (such as bacteria of the genera *Neisseriae, Bordetellae, Branhamellas, Haemophilus* and *Moraxellae*); or of the genera *Klebsiella, Pseudomonas, Burkolderia, Porphyromonas, Franciscella, Yersinia, Enterobacter, Salmonella, Shigella, Escherichia*, e.g. *E. coli*.

According to a preferred aspect, a vaccine composition according to the invention is in particular of use for treating or preventing an infection caused by *N. meningitidis*, such as meningitis caused by *N. meningitidis*, meningococcemia and complications which can derive therefrom, such as *purpura fulminans* and septic shock; and also arthritis and pericarditis caused by *N. meningitidis*.

It may be conventionally produced. In particular, a therapeutically or prophylactically effective amount of the constituents of the vaccine, namely the LPS and the lipidated TbpB, are combined with a carrier or with a diluent.

A vaccine according to the invention may comprise one or more lipidated TbpBs. Furthermore, it may comprise one or more additional vaccine antigen(s). Advantageously, they may be chosen from proteins of the bacterial species from which the LPS originates. In connection with this possibility, a vaccine composition according to the invention may also contain an additional, pharmaceutically acceptable, adjuvant for adjuvanting the additional vaccine antigen(s); nevertheless, this option is not the most attractive owing to the complexity thereof.

For this reason, according to one preferred embodiment, the vaccine according to the invention does not contain any adjuvant compound other than the LPS and the lipidated TbpB.

The amounts of LPS and of lipidated TbpB per vaccine dose which are sufficient to achieve the abovementioned aims, and which are effective from an immunogenic, prophylactic or therapeutic point of view, depend on certain parameters that include the individual treated (adult, adolescent, child or infant), the route of administration and the administration frequency.

Thus, the amount of LPS per dose which is sufficient to achieve the abovementioned aims is in particular between 5 and 500 µg, advantageously between 10 and 200 µg, preferably between 20 and 100 µg, entirely preferably between 20 and 80 µg or between 20 and 60 µg, limits included.

In the vaccine according to the invention the amount of lipidated TbpB per dose is between 5 and 500 µg, advantageously between 10 and 200 µg, preferably between 20 and 100 µg, entirely preferably between 20 and 80 µg or between 20 and 60 µg, limits included.

In the vaccine according to the invention the LPS: lipidated TbpB molar ratio is from $10^{-2}$ to $10^3$, advantageously from $10^{-1}$ to $10^2$, preferably from 1 to 50; most particularly preferably from 15 to 30, or approximately 20.

The term "dose" employed above should be understood to denote a volume of vaccine administered to an individual in one go—i.e. at T time. Conventional doses are of the order of a milliliter, for example 0.5, 1 or 1.5 ml; the definitive choice depending on certain parameters, and in particular on the age and the status of the recipient. An individual can receive a dose divided up into injections at several injection sites on the same day. The dose may be a single dose or, if necessary, the individual may also receive several doses a certain time apart—it being possible for this time apart to be determined by those skilled in the art.

The LPS and the lipidated TbpB used in the vaccine according to the invention may respectively be any LPS and lipidated TbpB described as being able to be used in the adjuvantation method according to the invention. The LPS and the lipidated TbpB may be formulated or prepared as described with regard to the method according to the invention.

It may be administered by any conventional route in the use in the prior art, e.g. in the vaccines field, in particular enterally or parenterally. The administration may be carried out as a single dose or as repeated doses a certain time apart. The route of administration varies as a function of various parameters, for example of the individual treated (condition, age, etc.).

Finally, the invention also relates to:
 a method for inducing in a mammal, for example a human, an immune response against a Gram-negative pathogenic bacterium, according to which an immunogenically effective amount of a vaccine according to the invention is administered to the mammal so as to induce an immune response, in particular a protective immune response against the Gram-negative pathogenic bacterium; and
 a method for prevention and/or treatment of an infection caused by a Gram-negative pathogenic bacterium, according to which a prophylactically or therapeutically effective amount of a vaccine according to the invention is administered to an individual in need of such a treatment.

The invention is illustrated by the experimental section as follows.

Experimental Data

1. Preparation of the Lipidated rTbpB
In the interest of simplifying the language, the term "rTbpB" will subsequently be simply indicated.
1.1. Production
Strain
The expression strain is the *E. coli* BL21 strain containing the pTG9219 plasmid. This plasmid contains in particular a kanamycin-selectable marker and the polynucleotide encoding the rTbpB from the *N. meningitidis* M982 strain, the sequence of which is as described in patent EP 586 266, fused to the *E. coli* R1pB (real lipoprotein B) signal sequence and placed under the control of the arabinose promoter (araB).
Culture
Three frozen samples of the *E. coli* BL21/pTG9219 strain (each 1 ml) are used to inoculate 3 liters of LB (Luria Broth) medium divided up in Erlenmeyer flasks. The incubation is continued for 15 to 18 h at 37° C.
This preculture is used to inoculate a fermenter containing TGM16 medium (9 g/L yeast extract, 0.795 g/L $K_2SO_4$, 3.15 g/L $K_2HPO_4$, 0.75 g/L NaCl, 0.005 g/L $CaCl_2.2H_2O$, 0.021 g/L $FeCl_3.6H_2O$, 0.69 g/L $MgSO_4.7H_2O$, 37.5 g/L salt-free casein acid hydrolysate) supplemented with 20 g/L glycerol, in a proportion of 10% (vol./vol).

The culturing is continued at 37° C. with shaking, at a pressure of 100 mbar and with an air feed of 1 L/min/L of culture, while readjusting, over time, the glycerol concentration to 20 g/L (e.g. at $OD_{600}$ of 15±2). When the $OD_{600}$ is between 21 and 27, the rTbpB expression is induced by adding arabinose so as to obtain a final concentration of 10 g/L. After one hour of induction, the culture is stopped by cooling to around 10° C.

The bacterial pellets are recovered by centrifugation and stored in the cold.

1.2. Purification

Extraction of Membranes Containing the rTbpB

LPS Extraction

A bacterial pellet equivalent to one liter of culture (approximately 72 g of microorganisms, wet weight) is thawed at a temperature of 20° C.+/−5° C. The thawed (or partially thawed) microorganisms are resuspended with 800 ml of a solution, at ambient temperature, of 50 mM Tris HCl, 5 mM EDTA, pH 8.0. 9 protease inhibitor tablets (7 complete Mini, EDTA free tablets; ROCHE ref. 11836170001+two complete, EDTA free tablets; ROCHE ref. 11836170001) are immediately added. Since some of the microorganisms lyze spontaneously, 4 µl of benzonase (1 IU of DNAse activity/ml final concentration; Merck ref. K32475095) are also added. The incubation is continued at +4° C. for 45 minutes with magnetic stirring after homogenization with a Turrax (15 sec.).

4 ml of 1M $MgCl_2$ are then added so as to be at a final concentration of 5 mM. The magnetic stirring is continued for 10 minutes. Centrifugation at 15 000 g for 45 minutes makes it possible to harvest the pellet (pellet P1; versus supernatant S1) containing the rTbpB protein.

A second extraction is carried out: homogenization with a Turrax in 800 ml of the 50 mM Tris HCl buffer containing 5 mM EDTA, pH 8.0, and stirring for 30 min. $MgCl_2$ (8 ml of a molar solution) is added. The incubation is continued for 10 minutes. The suspension is centrifuged at 15 000 g for 1 hour 30.

Bacterial Lysis

The pellet is resuspended with 1400 ml of 50 mM Tris HCl supplemented with 4 protease inhibitor tablets with 8 µl of benzonase. The solution is homogenized with a Turrax for 15 seconds. The lysis is carried out at +4° C. for 30 minutes through the addition of 14 ml (10 mg/ml final concentration) of lysozyme at 100 mg/ml in 25 mM Na acetate, 50% glycerol.

The suspension is centrifuged at 30 000 g for 30 minutes (pellet P2 containing the protein; versus supernatant S2 containing the contaminants of rTbpB). The pellet containing the membranes can be frozen at this stage.

Washing of Membrane Fragments

The lysis pellet P2 is taken up in 50 mM Tris HCl (1100 ml). After homogenization, (Turrax 15 seconds), it is washed for one hour at +4° C. A centrifugation is carried out as previously at 30 000 g for 30 minutes. The pellet (P3; versus supernatant S3) is frozen at −45° C. 50 mM Tris HCl buffer makes it possible to remove a small amount of protein (supernatant S3) and solubilizes only very little rTbpB.

The pellet P3 is taken up in 50 mM Tris HCl buffer containing 8M urea, pH 8.0 (800 ml). This buffer makes it possible to remove a part of the contaminating proteins without solubilizing the membranes containing the rTbpB. After homogenization (without using a Turrax), the solution is then stirred for one hour at +4° C. A centrifugation is carried out as previously at 30 000 g for 30 minutes, which makes it possible to obtain a membrane pellet which can be frozen.

Membrane Solubilization

The thawed membrane pellet is solubilized with 780 ml of 50 mM Tris HCl buffer containing 6 mM EDTA, 2M urea and 4% elugent, at pH 7.5. The presence of the detergent at 4% and of the 2M urea makes it possible to solubilize the pellet. The solution is stirred at +4° C. overnight (minimum 16 h). Centrifugation of the solution at 30 000 g (1 hour at +4° C.) leaves only a small pellet (P4) containing a few impurities. The supernatant S4 containing the rTbpB protein is recovered for loading on a first cation exchange column (QS I).

Purification by Anion Exchange Chromatography on Q SEPHAROSE at pH 7.5

Two successive chromatographies are carried out, the product of the first chromatography is collected and then subsequently loaded, after a dialysis step, on a second chromatography column which uses different conditions (absence of EDTA).

$1^{st}$ Chromatography, in the Presence of EDTA (Chromatography QS I)

A column of 600 ml (K50, diameter 20 $cm^2$) of Q SEPHAROSE Fast Flow gel (ref. 17-0510-01 GE Healthcare) is mounted, tamped in equilibration buffer, 50 mM Tris HCl containing 6 mM EDTA, 2M urea and 1% ELUGENT, at pH 7.5, at the flow rate of 8 ml/minute.

The supernatant S4 (approximately 845 ml) is loaded at the flow rate of 6 ml/minute. The direct eluate (part which does not attach to the column during loading of the sample) contains the protein of interest, rTbpB. The eluate (1150 ml) is taken and then dialyzed at +4° C. (for 6 days) against 6 liters of 50 mM Tris HCl buffer containing 2M urea and 1% elugent, pH 7.5, in order to reduce the EDTA concentration to 1 mM and to remove the NaCl.

$2^{nd}$ Chromatography (QS II), Without EDTA

A K50 column of 490 ml of new Q SEPHAROSE Fast Flow gel is equilibrated in 50 mM Tris HCl buffer containing 2M urea and 1% ELUGENT, pH 7.5.

The dialyzed solution (1080 ml) is loaded on the column (flow rate 6 ml/minute); then 5 saline elution steps in this same buffer are carried out: 20 mM, 50 mM, 100 mM, 250 mM and 1M NaCl (working flow rate 6 ml/minute). The rTbpB protein is eluted from the column at two salt concentrations (50 mM and 100 mM). The 50 mM elution fraction is the fraction of interest, since the rTbpB protein therein is the purest and is present in a greater amount (2.6 times more protein than in the 100 mM NaCl fraction).

The pH of the fraction corresponding to the 50 mM NaCl elution peak is decreased, with magnetic stirring, to pH 5.5 by adding 1.7N acetic acid. The solution (860 ml) is dialyzed against 5 liters of 10 mM sodium acetate buffer containing 1M urea and 0.2% ELUGENT, pH 5.5 (24 hours at +4° C.) and then against 4 liters of 10 mM sodium acetate buffer containing 1M urea and 0.2% ELUGENT, pH 5.5 (17 hours at +4° C.).

Purification by Cation Exchange Chromatography on SP SEPHAROSE (SP1) at pH 5.5

A K50 column or 100 ml of new SP SEPHAROSE Fast Flow gel (Ge Healthcare, ref. 17-0729-01) is equilibrated in 10 mM sodium acetate buffer containing 1M urea and 0.2% ELUGENT, pH 5.5.

The dialyzed protein solution (850 ml) is loaded on the column (flow rate 6 ml/minute). Then, five saline elution steps are carried out: 50 mM, 100 mM, 250 mM, 500 mM and 1M NaCl, in the buffer mentioned above.

The rTbpB protein is eluted exclusively in the 250 mM NaCl fraction and the low-molecular-weight contaminants are eliminated essentially in the direct eluate (40%). Approximately 35 mg of purified rTbpB are thus obtained.

Dialysis and Concentration of the SPI Product (250 mM Fractions)

The fractions corresponding to the 250 mM elution peak of the SPI column are combined (volume 274 ml). The pH of the solution is brought back up to pH 7.3 by adding, with stirring, approximately 800 μl of 0.5N NaOH. The solution is dialyzed at +4° C. (Spectra Por 1: cutoff threshold 6-8000 D) against two 10 liter baths of PBS containing 0.2% elugent, pH 7.1 (66 hours and 22 hours).

The dialyzate is concentrated to a volume of 21.1 ml by frontal diafiltration concentration on a 30 kD Amicon membrane in PBS (ref. PBTK06510).

The concentrate obtained is then again dialyzed against 2 liters of PBS containing 0.2% elugent, pH 7.1 (Slide A Lyser ref. 66810: cutoff threshold 10 kD).

The solution is then filtered aseptically through a 0.22 μm Millex filter with Durapore membrane (Millipore ref. SLGV 033RS). The purified rTbpB protein batch obtained is frozen at −80° C. The protein concentration is 1642 μg/ml.

1.3. Preparation of rTbpB for Injection

The rTbpB solution obtained in section 1.2. is treated by adsorption on Bio-Beads™ SM-2 in order to remove the excess Elugent™ detergent (surfactant constituted of alkyl glucosides) which could destabilize the LPS L8 liposomes.

Activation of Bio-Beads™

Approximately 2.5 ml of methanol are added to 500 mg of Bio-Beads™ and the mixture is homogenized intermittently for 15 min at ambient temperature. After a settling-out period, the supernatant is removed. This washing operation is repeated twice.

Approximately 5 ml of ultrafiltered sterile water are then added and the mixture is homogenized intermittently for 15 min at ambient temperature. After a settling-out period, the supernatant is removed. This washing operation is repeated twice.

Approximately 5 ml of PBS are then added and the mixture is homogenized intermittently for 15 min at ambient temperature. It is stored at 5° C. and used the same day.

At the end, the weight of the Bio-Beads™ has increased by a factor R (equal to approximately 1.2).

Removal of the Detergent by Adsorption on Bio-Beads™

The rTbpB solution obtained in section 1.2. contains 2 mg/ml of Elugent™. The amount of Bio-Beads™ that has to be used is determined according to the amount of Elugent™ to be removed.

For one ml of the rTbpB solution obtained in section 1.2., 29×R mg of activated Bio-Beads™ are added. The mixture is vigorously stirred for one hour at ambient temperature. The maximum amount of liquid is then recovered and a final concentration of 0.001% of merthiolate is added thereto. The whole process is carried out under sterile conditions.

2. Preparation of the Purified LPS L8

Culturing

Eight ml of frozen sample of *N. meningitidis* strain A1, serotype A, known to exclusively express immunotype L8 are used to inoculate 800 ml of Mueller-Hinton medium (Merck) supplemented with 4 ml of a solution of glucose at 500 g/l and divided up in Erlenmeyer flasks. The culturing is continued with shaking at 36±1° C. for approximately 10 hours.

400 ml of a solution of glucose at 500 g/l and 800 ml of a solution of amino acids are added to the preculture. This preparation is used to inoculate a fermentor containing Mueller-Hinton medium, at an $OD_{600nm}$ close to 0.05. The fermentation is continued at 36° C., at pH 6.8, 100 rpm, $pO_2$ 30% under an initial airstream of 0.75 l/min/l of culture.

After approximately 7 hours ($OD_{600nm}$ of approximately 3), Mueller-Hinton medium is added at a rate of 440 g/h. When the glucose concentration is less than 5 g/l, the fermentation is stopped. The final $OD_{600nm}$ is commonly between 20 and 40. The cells are harvested by centrifugation and the pellets are frozen at −35° C.

Purification

The pellets are thawed and suspended with 3 volumes of 4.5% (vol./vol.) phenol with vigorous stirring for 4 hours at approximately 5° C. The LPS is extracted by phenol treatment.

The bacterial suspension is heated to 65° C. and then mixed vol./vol. with 90% phenol, with vigorous stirring for 50-70 min at 65° C. The suspension is subsequently cooled to ambient temperature and then centrifuged for 20 min at 11 000 g. The aqueous phase is removed and stored, while the phenolic phase and the interphase are harvested so as to be subjected to a second extraction.

The phenolic phase and the interphase are heated to 65° C. and then mixed with a volume of water equivalent to that of the aqueous phase previously removed, with vigorous stirring for 50-70 min at 65° C. The suspension is subsequently cooled to ambient temperature and then centrifuged for 20 min at 11 000 g. The aqueous phase is removed and stored, while the phenolic phase and the interphase are harvested so as to be subjected to a third extraction identical to the second.

The three aqueous phases are dialyzed separately, each against 40 l of water. The dialyzates are then combined. One volume of 20 mM Tris, 2 mM $MgCl_2$ is added to 9 volumes of dialyzate. The pH is adjusted to 8.0±0.2 with 4N sodium hydroxide.

Two hundred and fifty international units of DNAse are added per gram of pellet. The pH is adjusted to 6.8±0.2. The preparation is placed at 37° C. for approximately 2 hours with magnetic stirring, and then subjected to filtration through a 0.22 μm membrane. The filtrate is purified by passing it through a SEPHACRYL S-300 column (5.0×90 cm; Pharmacia™).

The fractions containing the LPS are combined and the $MgCl_2$ concentration is increased to 0.5M by adding powdered $MgCl_2.6H_2O$, with stirring.

While continuing the stirring, dehydrated absolute alcohol is added to give a final concentration of 55% (vol./vol.). The stirring is continued overnight at 5±2° C., and then centrifugation is carried at 5000 g for 30 min at 5±2° C. The pellets are resuspended with at least 100 ml of 0.5M $MgCl_2$ and then subjected to a second alcoholic precipitation identical to the preceding one. The pellets are resuspended with at least 100 ml of 0.5M $MgCl_2$.

The suspension is subjected to a gel filtration as previously described. The fractions containing the LPS are combined and filtration-sterilized (0.8-0.22 μm) and stored at 5±2° C.

This purification method makes it possible to obtain approximately 150 mg of LPS L8 per liter of culture.

3. Production of an Endotoxoid L8 (LPS L8 Detoxified by Complexation with a Peptide Analog of Polymyxin B)

This endotoxoid is prepared as described in patent application WO 06/108586. Briefly, one volume of a solution of purified LPS L8 at 1 mg/ml, sterilized by filtration through a 0.22 μm membrane, is mixed with one volume of a solution of SAEP2-L2 peptide at 1 mg/ml, sterilized by filtration through a 0.22 μm membrane.

The SAEP2-L2 peptide is a peptide with an antiparallel dimeric structure, of formula:

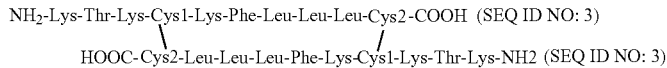

NH₂-Lys-Thr-Lys-Cys1-Lys-Phe-Leu-Leu-Leu-Cys2-COOH (SEQ ID NO: 3)
HOOC-Cys2-Leu-Leu-Leu-Phe-Lys-Cys1-Lys-Thr-Lys-NH2 (SEQ ID NO: 3)

A precipitate forms immediately. Mixing is carried out for 5 min at ambient temperature, and then the mixture is left to stand overnight at 4° C. The precipitate is harvested by centrifugation at 3000 rpm for 10 min. The pellet is washed 5 times with one volume of pyrogen-free sterile water, pH 7.2. Finally, the pellet is resuspended in 10 mM Tris buffer containing 150 mM NaCl and TWEEN 80, pH 7.4, so as to obtain a suspension at 1 mg/ml, calculated based on the wet weight of the precipitate. The suspension is stored at 4° C.

4. Preparation of an Endotoxoid L8+rTbpB Mixture rTbpB in PBS (obtained as described in section 1.3.) is mixed with endotoxoid (section 3.) in a weight:weight ratio equal to 1. The volume is then adjusted with 10 mM Tris buffer containing 150 mM NaCl and 0.05% Tween 80 so as to obtain a preparation in which each of the components is at a concentration of 80 µg/ml.

5. Preparation of [LPS L8] Liposomes by Detergent Dialysis 5.1. Preparation of Liposomes The LPS L8 liposomes are prepared by detergent dialysis. Briefly, the lipids (EDOPC:DOPE) are made into the form of a lipid film and taken up in 10 mM Tris buffer, and then dispersed in the presence of 100 mM of octyl-β-D-glucopyranoside (OG) (Sigma-Aldrich ref. O8001) and filtered sterilely. The LPS L8 in 100 mM OG is added sterilely. The lipids/LPS/OG mixture is then dialyzed against 10 mM Tris buffer in order to remove the OG and to form the liposomes.

Protocol

A lipid preparation in chloroform, of the lipids that will be used to produce the liposomes, is prepared. A dry film is obtained by complete evaporation of the chloroform.

A dry film of 1,2-dioleoyl-sn-glycero-3-ethylphosphocholine (EDOPC or ethyl-DOPC) and of 1,2-dioleoyl-sn-glycero-3-phosphoethanolamine (DOPE) in an EDOPC:DOPE molar ratio of 3 to 2 is obtained by mixing 12.633 ml of a solution of EDOPC (Avanti Polar Lipids ref. 890704) at 20 mg/ml in chloroform and 7.367 ml of a solution of DOPE (Avanti Polar Lipids ref. 850725) at 20 mg/ml in chloroform, and evaporating off the chloroform until it has completely disappeared.

The dry film is taken up with 30 ml of 10 mM Tris buffer, pH 7.0, so as to obtain a suspension containing 13.333 mg of lipids/ml (8.42 mg/ml of EDOPC and 4.91 mg/ml of DOPE). The suspension is stirred for 1 hour at ambient temperature and then sonicated for 5 min in a bath.

3.333 ml of a sterile 1M solution of octyl-β-D-glucopyranoside (OG) (Sigma-Aldrich ref. O8001) in 10 mM Tris buffer, pH 7.0, are then added, still with stirring, so as to obtain a clear suspension of lipids at 12 mg/ml, 100 mM OG and 10 mM Tris buffer. The stirring is continued for 1 h at ambient temperature on a platform shaker. Filtration is then carried out sterilely through a Millex HV 0.45 µm filter.

A composition is prepared, under sterile conditions, by bringing together LPS and lipids in a lipids:LPS molar ratio of 250 (0.160 mg/ml of LPS L8, 9.412 mg/ml of lipids and 100 mM of OG). 40 ml of such a composition are obtained from mixing the following preparations:

2.005 ml of 10 mM Tris buffer, pH 7.0; 0.223 ml of 100 mM OG in 10 mM Tris; 31.373 ml of the EDOPC:DOPE suspension having a molar ratio of 3:2, at 12 mg/ml in 100 mM OG, 10 mM Tris; and 6.4 ml of a sterile suspension of LPS L8 at 1 mg/ml in 100 mM OG, 10 mM Tris.

After stirring for one hour at ambient temperature, the suspension is transferred sterilely into 4 sterile 10 ml dialysis cassettes. Each cassette is dialyzed 3 times (24 hrs-24 hrs-72 hrs) against 200 volumes of 10 mM Tris, pH 7.0, i.e. 2 l.

The liposomes are recovered under sterile conditions. The increase in volume after dialysis is approximately 30%.

Merthiolate and NaCl are added to this preparation so as to obtain a preparation of liposomes in 10 mM Tris, 150 mM NaCl, pH 7.0, 0.001% merthiolate, which ultimately contains approximately 110 µg/ml of LPS and 7 mg/ml of lipids, of which there are approximately 4.5 mg/ml of EDOPC and approximately 2.5 mg/ml of DOPE (theoretical concentrations).

The LPS liposomes are stored at +5° C.

5.2. Preparation of the Injectable Materials

The liposomes are adjusted to the required LPS concentration (in particular required for the immunogenicity test) in 10 mM Tris, 150 mM NaCl, pH 7.4. The merthiolate concentration is maintained at 0.001%.

6. Preparation of an [LPS L8] Liposomes+rTbpB Mixture rTbpB in PBS (section 1.3.) is mixed with [LPS L8] liposomes (section 5.) in an rTbpB:LPS weight:weight ratio equal to 1. The volume is then adjusted with 10 mM Tris buffer containing 150 mM NaCl, pH 7.4, so as to obtain a preparation in which each of the components (rTbpB and LPS) is at a concentration of 80 µg/ml. The merthiolate concentration is maintained at 0.001%.

7. Preparation of [LPS L8+rTbpB] Liposomes (or LPS L8 Proteoliposomes)

7.1. Preparation of Proteoliposomes

The LPS L8 proteoliposomes are prepared by removal of detergent with BioBeads™.

The lipids (EDOPC:DOPE) are first of all made into the form of a film and taken up in 10 mM Tris buffer, and then dispersed in 100 mM OG and filtered under sterile conditions, as described in section 5.

A mixture made up of rTbpB, LPS and lipids in a lipids: LPS molar ratio of 250 and in an rTbpB:LPS weight:weight ratio of 1 is then prepared under sterile conditions (0.160 mg/ml of rTbpB, 0.160 mg/ml of LPS L8, 9.412 mg/ml of lipids and 100 mM of OG): the LPS L8 in 100 mM OG is added sterilely to the dispersed lipids, and also the rTbpB as prepared in section 1.2.

The lipids/LPS/OG mixture is then treated with BioBeads™ in order to remove the Elugent™ and the OG and thus to form the liposomes.

After stirring for one hour at ambient temperature, activated BioBeads™ are added as described in section 1.3., in a proportion of 0.63 g per ml of mixture. After stirring for one hour at ambient temperature, the LPS proteoliposomes are recovered under sterile conditions and are subsequently stored at +5° C.

[Note: The [rTbpB] proteoliposomes are prepared in the same way, but without the addition of LPS.]

7.2. Preparation of Injectable Materials

The proteoliposomes are adjusted in 150 mM NaCl and 0.001% merthiolate so as to obtain the required concentrations of rTbpB and LPS (in particular, implementation of the immunogenicity tests).

8. Quantification of the Lipids, of the LPS and of the rTbpB in Liposomes
8.1. Assaying of Lipids by HPLC-UV
Preparation of the Standard Range and of the Samples to be Analyzed A stock solution containing 1 mg/ml, in chloroform, of each of the EDOPC and DOPE lipids is prepared and is subsequently diluted to $\frac{1}{10}^{th}$ by adding an acetonitrile/water (90/10) mixture. This stock solution is used to prepare the standard range of 2 to 50 µl/ml by dilution in acetonitrile/water mixture.

The samples to be analyzed are diluted in acetonitrile/water so as to have a theoretical final concentration of approximately 10 µg/ml.
Analytical Conditions A Zorbax C18 Extend, 3; 5 µm, 3×150 mm, 80A column (Agilent reference 763954-302) is used, and for the mobile phase, an acetonitrile/water/trifluoroacetic acid (TFA) mixture in the volume proportions 850/150/1 is used. The column is pre-conditioned according to the following process:
  flow rate at 0.25 ml/min for 20 minutes (P=21 bar)
  flow rate at 0.5 ml/min for 20 minutes (P=42 bar)
  flow rate at 0.75 ml/min for 20 minutes (P=60 bar)
  flow rate at 1 ml/min for 20 minutes (P=80 bar)

The measurements are carried out at 60° C., by injecting 10 µl of the preparation at a mobile-phase flow rate of 1 ml/min. The analytes are detected at OD 200 nm.
  DC-chol average retention time: 1.6 minutes
  EDOPC average retention time: 7.7 minutes
  DOPC average retention time: 9.9 minutes
  DOPE average retention time: 11.5 minutes
  Cholesterol average retention time: 13.4 minutes
8.2. Assaying of LPS by HPAEC-PAD The principle of the assay consists in subjecting the LPS to an acid hydrolysis which releases one molecule of KDO per molecule of LPS; then in separating this free KDO from the rest and in quantifying it by high performance ion exchange chromatography with pulsed amperometric detection (HPAEC-PAD).
Preparation of the Standard Range and of the Samples to be Assayed The following are prepared in a final volume of 400 µl: a blank and a standard range of KDO of between 42.5 and 1700 ng/ml; which corresponds to a standard range of LPS of between 613 and 24507 ng of LPS/ml. The blank and each of the samples of the range also contain an amount of lipids and/or of detergent substantially equivalent to that present in the samples to be assayed; that is to say, e.g. 0.7 mg/ml of a mixture of EDOPC and of DOPE in a molar ratio of 3:2 and also of 0.2 mM octyl glucoside.

The samples to be assayed are prepared in a final volume of 400 µl by dilution, e.g. to $\frac{1}{10}^{th}$, of a preparation of liposomes at a starting theoretical LPS concentration of 100 µg/ml.
Acid Hydrolysis 100 µl of a hydrolysis solution containing 5% acetic acid and glucuronic acid at 20 µg/ml (compound used as internal standard) prepared extemporaneously are introduced into the standard range+blank samples and into the samples to be assayed. The hydrolysis is allowed to continue for 1 h at 100° C. and is then stopped by centrifugation at 5° C. for 5 min.
Extraction of the Lipids and of the Detergent 500 µl of purified water are added to the hydrolysis product, followed by 2 ml of a 2/1 mixture of chloroform/methanol, and the mixture is vortexed for 30 sec. It is centrifuged at 4500 rpm for 10 min. The aqueous phases are taken, dried at 45° C. for 2 hours under a nitrogen stream at 0.5 bar and taken up with 400 µl of water.

HPAEC-PAD Assay

This technique is implemented on an HPAEC system (Dionex™) using the Dionex™ Chromeleon management software for the data acquisition and reprocessing. The chromatography column (Carbopac PA1×250 mm (Dionex™ reference 035391)) is subjected to a temperature of 30° C. The column is equilibrated with an eluting solution (75 mM NaOH, 90 mM NaOAc) and pre-conditioned according to the following scheme:
  flow rate at 0.20 ml/min for 20 minutes (P=270 psi)
  flow rate at 0.4 ml/min for 20 minutes (P=540 psi)
  flow rate at 0.6 ml/min for 20 minutes (P=800 psi)
  flow rate at 0.8 ml/min for 20 minutes (P=1055 psi)
  flow rate at 1 ml/min for 20 minutes (P=1300 psi)

100 µl of a sample are injected onto the column at an elution flow rate of 1 ml/min for 22 min.

The amount of KDO present in the sample is determined by integration of the KDO peak of the chromatogram. Since one mole of KDO is released per mole of LPS, it is possible to determine the concentration of LPS present in the initial preparation.
8.3. Assaying of rTbpB in Liposomes Since proteins cannot be assayed in the presence of lipids, the assay is carried out directly by SDS-PAGE on a 4-12% criterion Bis Tris 18-well gel (Biorad), in 1×C MOPS running buffer (Biorad). The gel is stained with GelCode (Pierce) and the rTbpB concentrations are deduced by densitometry from a standard range loaded on a gel.
9. Immunogenicity Studies in Rabbits and Mice The various formulations tested were produced as described in one of the preceding sections.
9.1. Immunization of Rabbits
Experiment No. 1

Twenty-four 7-week-old female NZ-KBL rabbits (Charles River Lab.) are divided up into 5 test groups of four and 2 control groups of two.

The female rabbits of each group receive, in a volume of 0.5 ml, divided up into 2 concomitant intramuscular injections in the legs, at D0 and D21:
Group 1 10 mM Tris, 150 mM NaCl, 0.05% TWEEN 80, pH 7.4 (negative control)
Group 2 liposomes as prepared in Tris NaCl buffer, pH 7.0
Group 3 40 µg of endotoxoid L8 prepared as described in section 3, in Tris NaCl buffer, 0.05% TWEEN 80, pH 7.4
Group 4 40 µg of LPS L8 formulated in liposomes, in Tris NaCl buffer, pH 7.0
Group 5 40 µg of rTbpB and 40 µg of LPS L8, formulated in liposomes, in Tris NaCl/PBS buffer, pH 7.0
Group 6 40 µg of rTbpB in PBS buffer
Group 7 40 µg of rTbpB mixed with 40 µg of LPS L8 formulated in liposomes, adjusted in Tris NaCl buffer, pH 7.0.

A blood sample is taken from the animals for analysis at D-7, D21 (before the second injection) and at D42.
Experiment No. 2

Twenty-two 7-week-old female NZ-KBL rabbits (Charles River Lab.) are divided up into 5 test groups of four and one control group of two.

The female rabbits of each group receive, in a volume of 0.5 ml, divided up into 2 concomitant intramuscular injections in the legs, at D0, D21 and D42:
Group A 40 µg of rTbpB mixed with 40 µg of LPS L8 formulated in liposomes, in Tris NaCl/PBS buffer, pH 7.0.
Group B 10 µg of rTbpB mixed with 40 µg of LPS L8 formulated in liposomes, in Tris NaCl/PBS buffer, pH 7.0.
Group C 2.5 µg of rTbpB mixed with 40 µg of LPS L8 formulated in liposomes, in Tris NaCl/PBS buffer, pH 7.0.

Group D 40 μg of rTbpB mixed with 40 μg of endotoxoid L8 prepared as described in section 3., adjusted in Tris NaCl buffer, 0.05% TWEEN 80, pH 7.4.

Group E 40 μg of LPS L8 formulated in liposomes, in Tris NaCl buffer, pH 7.0.

Group F liposomes in Tris NaCl buffer, pH 7.0.

A blood sample is taken from the animals for analysis at D-2, D42 (before the second injection) and at D56.

9.2. Immunizations of Mice

One hundred and ten 7-week-old female CD1 mice (Charles River Lab.) are divided up into 10 test groups of ten and 2 control groups of five.

The mice of each group receive, subcutaneously and in a volume of 200 μl, at D0, D21 and D35:

Group 1 10 mM Tris, 150 mM NaCl, TWEEN 80, pH 7.4 (negative control)

Group 2 liposomes as prepared in Tris NaCl buffer, pH 7.0

Group 3 10 μg of endotoxoid L8 prepared as described in section 3, in Tris NaCl buffer, 0.05% TWEEN 80, pH 7.4

Group 4 10 μg of LPS L8 formulated in liposomes, in Tris NaCl buffer, pH 7.0

Group 5 10 μg of rTbpB and 10 μg of LPS L8 formulated in liposomes, in Tris NaCl/PBS buffer, pH 7.0

Group 6 10 μg of rTbpB in PBS buffer

Group 7 10 μg of rTbpB mixed with 10 μg of LPS L8 formulated in liposomes, adjusted in Tris NaCl buffer, pH 7.0

Group 8 10 μg of rTbpB adjuvanted with incomplete Freund's adjuvant and 10 μg of CpG 1826 oligonucleotide (5'-TC-CATGACGTTCCTGACGTT-3' [SEQ ID NO: 4]; Coley Pharm Group, Langenfeld, Germany), in PBS buffer Group 9 10 μg of lipidated rTbpB formulated in liposomes Group 10 10 μg of rTbpB Cter, in PBS buffer Group 11 10 μg of rTbpB Cter, in PBS buffer, mixed with 10 μg of LPS L8 formulated in liposomes, in Tris NaCl buffer, pH 7.0

Group 12 10 μg of rTbpB Cter adjuvanted with incomplete Freund's adjuvant and 10 μg of CpG 1826 oligonucleotide, in PBS buffer The rTbpB Cter of groups 10, 11 and 12 is a truncated TbpB devoid of the N-terminal portion. It has the characteristic of not being lipidated.

A blood sample is taken from the animals for analysis at D42.

9.3. Assaying of Anti-LPS Antibodies by ELISA

This assay is automated (Staccato automation system, Caliper) according to the following protocol:

The wells of Dynex™ 96-well plates are impregnated with 1 μg of LPS L8 in IX PBS (phosphate buffered saline) buffer, pH 7.1, 10 mM $MgCl_2$, and the plates are incubated for 2 hours at 37° C. and then overnight at 4° C. The plates are blocked by adding, to the wells, 150 μl of PBS containing 0.05% of TWEEN 20 and 1% (weight/vol) of skimmed milk powder (PBS-TWEEN-milk). The plates are incubated for 1 hour at 37° C.

Serial doubling dilutions of the test samples are prepared in PBS-0.05% TWEEN-1% milk. The plates are incubated for 90 min at 37° C. and then washed 3 times with PBS+TWEEN 20 at 0.05%.

A peroxidase-anti-mouse IgG or peroxidase-anti-rabbit IgG conjugated in PBS-TWEEN-milk is added to the wells and the plates are incubated for 90 min at 37° C. The plates are washed three times. 100 μl of a ready-to-use solution of TMB (3,3',5,5'-tetramethylbenzidine, substrate for peroxidase) are distributed per well. The plates are incubated in the dark for 20 min at ambient temperature. The reaction is stopped by adding 100 μl of 1M HCl per well.

The optical density is measured at 450-650 nm with an automatic reader (Multiskan Ascent). In the absence of standard, the antibody titers are determined as being the reciprocal dilution giving an optical density of 1.0 on a tendency curve (CodUnit software). The antibody detection threshold is 1.3 $\log_{10}$ ELISA unit. For each titer below this threshold, an arbitrary value of 1.3 $\log_{10}$ is assigned.

9.4. Assaying of Anti-rTbpB Antibodies by ELISA

The anti-TbpB IgGs are assayed manually according to the following protocol:

The wells of Dynex™ 96-well plates are impregnated with 200 ng of complete TbpB in 0.05M sodium carbonate buffer, pH 9.6 (Sigma). The plates are incubated overnight at 4° C. The plates are blocked by adding, to the wells, 150 μl of PBS, pH 7.1, containing 0.05% of TWEEN 20 and 1% (weight/vol.) of skimmed milk powder (PBS-TWEEN-milk). The plates are incubated for 1 hour at 37° C.

Serial doubling dilutions of the test samples are prepared in PBS-0.05% TWEEN-1% milk, and then added to the wells (starting from the 1/100 or 1/100 dilutions). The plates are incubated for 90 min at 37° C. and then washed 3 times with PBS+TWEEN 20 at 0.05%.

A peroxidase-anti-mouse IgG conjugate (Jackson; diluted to 1/4000 in PBS-TWEEN-milk) or a peroxidase-anti-rabbit IgG conjugate (Sigma; diluted to 1/40 000 in PBS-TWEEN-milk) is added to the wells and the plates are incubated for 90 min at 37° C. The plates are washed three times. 100 μl of a ready-to-use solution of TMB (3,3',5,5'-tetramethylbenzidine, substrate for peroxidase) (Tebu) are distributed per well. The plates are incubated in the dark for 30 min at ambient temperature. The reaction is stopped by adding 100 μl of 1M HCl per well.

The optical density (OD) is measured at 450 nm-650 nm with an ELISA plate reader (Spectra Max). The blanks (mean of the negative controls) are subtracted from the data. The IgG titers are calculated with the Codunit software for the OD values between 0.2 and 3, from the titration curve (rabbit hyperimmune standard serum deposited on each plate). The IgG titer of this standard, expressed in ELISA units, was previously defined on the basis of several independent tests, and corresponds to the log 10 value of the arithmetic mean of the inverse of the dilution giving an OD of 1 in each of these tests.

The detection threshold value is 10 ELISA units (1 log 10). The final titers are expressed as log 10 values.

9.5. Measurement of the Bactericidal Activity of the Sera

The sera are inactivated by heating at 56° C. for 30 min. 10 serial 2-fold dilutions are carried out in gelatin-containing Dulbecco's PBS with calcium and magnesium ions. The dilutions are carried out in a 96-well plate for a final volume of 50 μl per well.

Twenty-five μl of a culture of N. meningitidis in the exponential phase ($4 \times 10^3$ CFU/ml) in BHI medium supplemented or not supplemented with 50 μM of Desferal (agent which chelates iron in free form), and also 25 μl of baby rabbit complement at 1/1.5, are added to each well. The plate is incubated for one hour at 37° C., with shaking Fifty μl of the mixture of each well are then deposited on bioMérieux Mueller-Hinton agar plates and incubated overnight at 37° C. under 10% $CO_2$. The number of clones is counted.

There are Three Controls:

bacteria+baby rabbit complement, without test serum ("complement" control);

bacteria+inactivated baby rabbit complement, without test serum ("microorganism" control); and bacteria+inactivated baby rabbit complement+test serum (serum control).

The bactericidal titer is expressed as the inverse of the dilution giving 50% bacterial death by comparison with the "complement" control.

For each group, the conversion rate is established as being the ratio GMT at D-day after administration:GMT at D-day before administration. It is considered that there is some bactericidal activity when the conversion rate is superior or equal to 4.

9.6. Results and Discussion

ELISAs

FIG. 1 gives the ELISA titers expressed as $\log_{10}$ of the anti-LPS L8 IgGs of the rabbit sera of groups 3, 4, 5 and 7, derived from experiment No. 1. In white, the titers of the sera before immunization; shaded, those of the sera of which samples were taken at D21 after the first immunization; and shaded/hatched, those of the sera of which samples were taken at D42.

Figure 2:
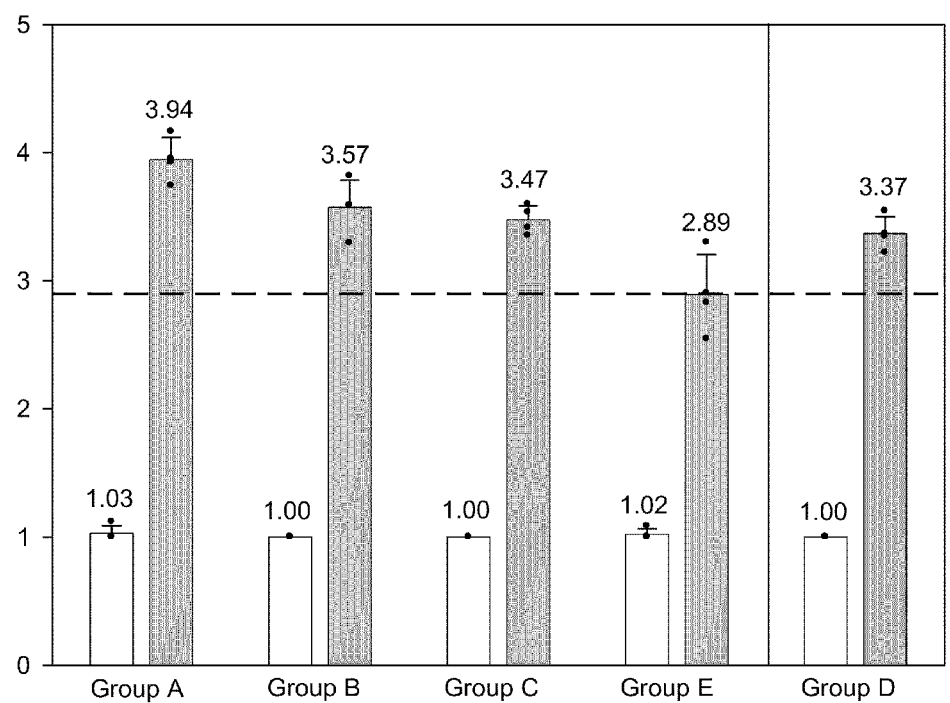

FIG. 2 gives the ELISA titers expressed as $\log_{10}$ of the anti-LPS L8 IgGs of the rabbit sera of groups A to E, derived from experiment No. 2. In white, the titers of the sera before immunization; and shaded, those of the sera of which samples were taken at D56 after the first immunization.

Figure 3:
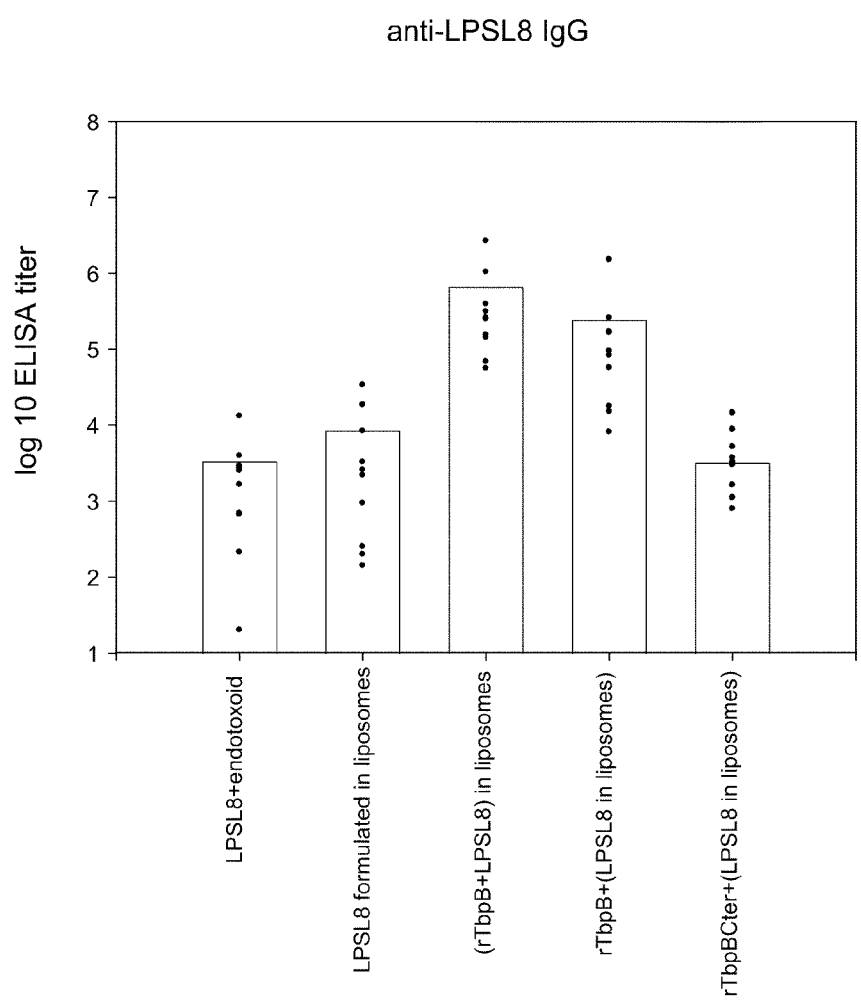

FIG. 3 gives the ELISA titers expressed as $\log_{10}$ of the anti-LPS L8 IgGs of the mouse sera.

FIGS. 4A and 4B give, respectively, the ELISA titers expressed as $\log_{10}$ of the anti-LPS L8 IgG1s and anti-LPS L8 IgG2as of the mouse sera.

Figure 5:
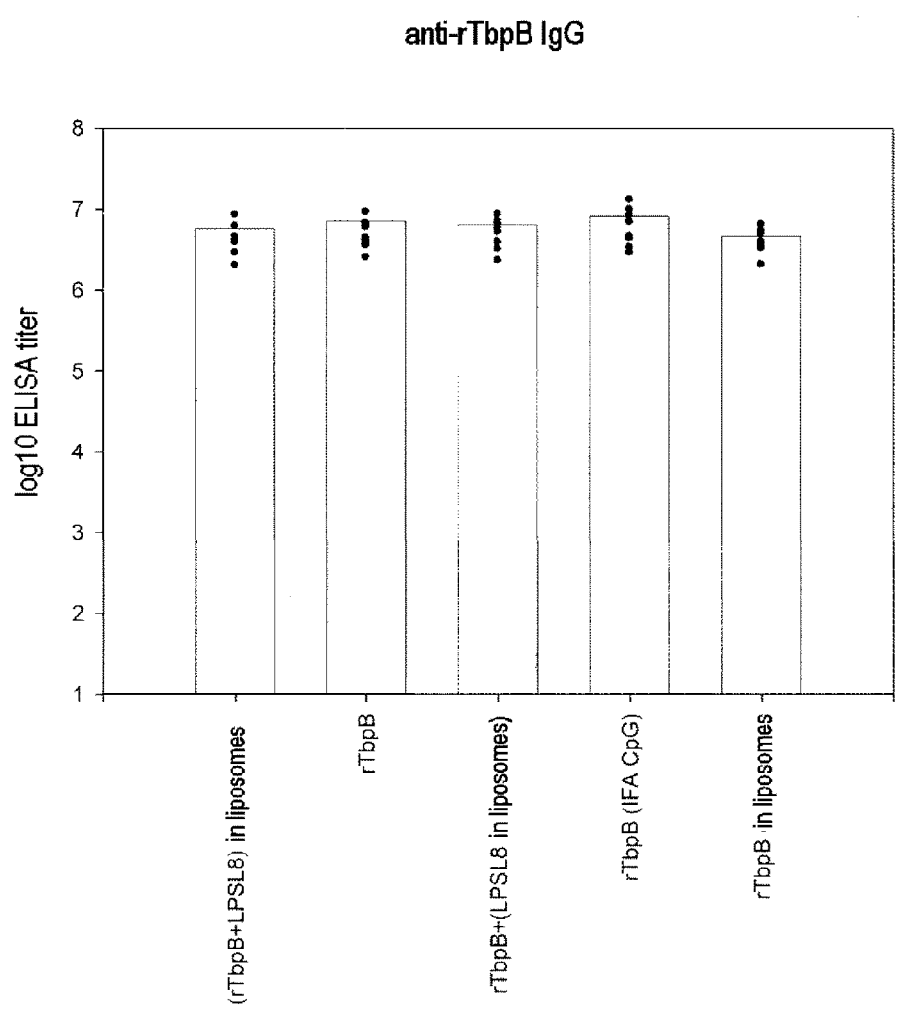

FIG. 5 gives the ELISA titers expressed as $\log_{10}$ of the anti-TbpB IgGs of the mouse sera.

Figure 6B:
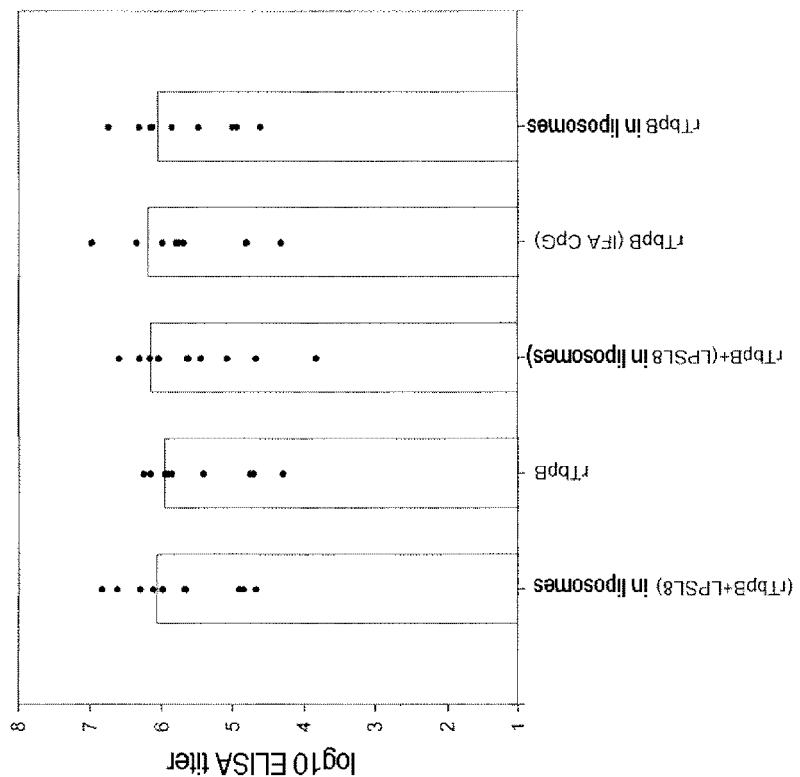
Figure 6A:
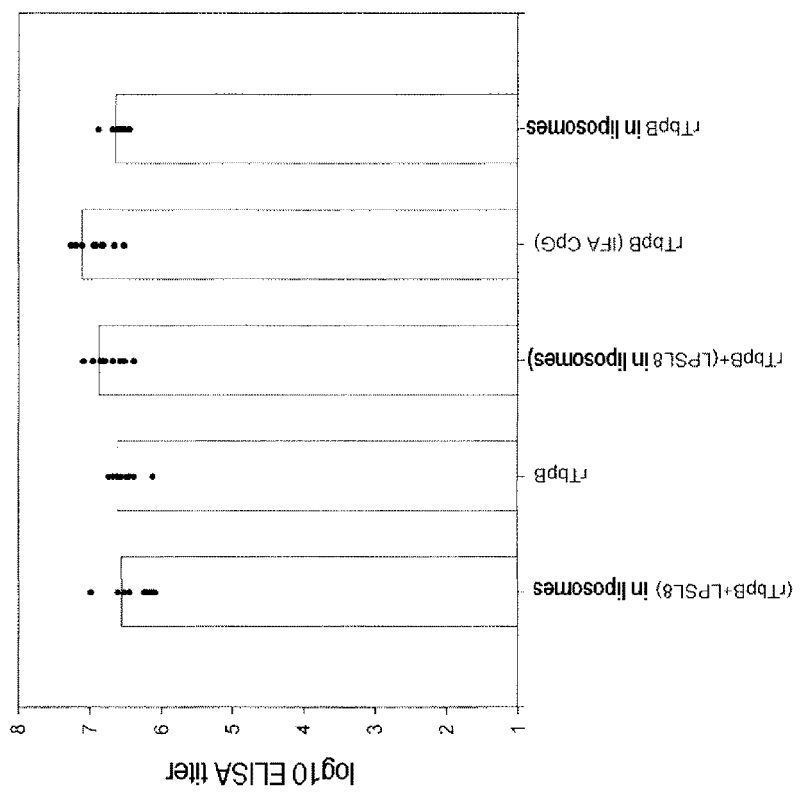

FIGS. 6A and 6B give, respectively, the ELISA titers expressed as $\log_{10}$ of the anti-TbpB IgG1s and anti-TbpB IgG2as of the mouse sera.

Figure 7:
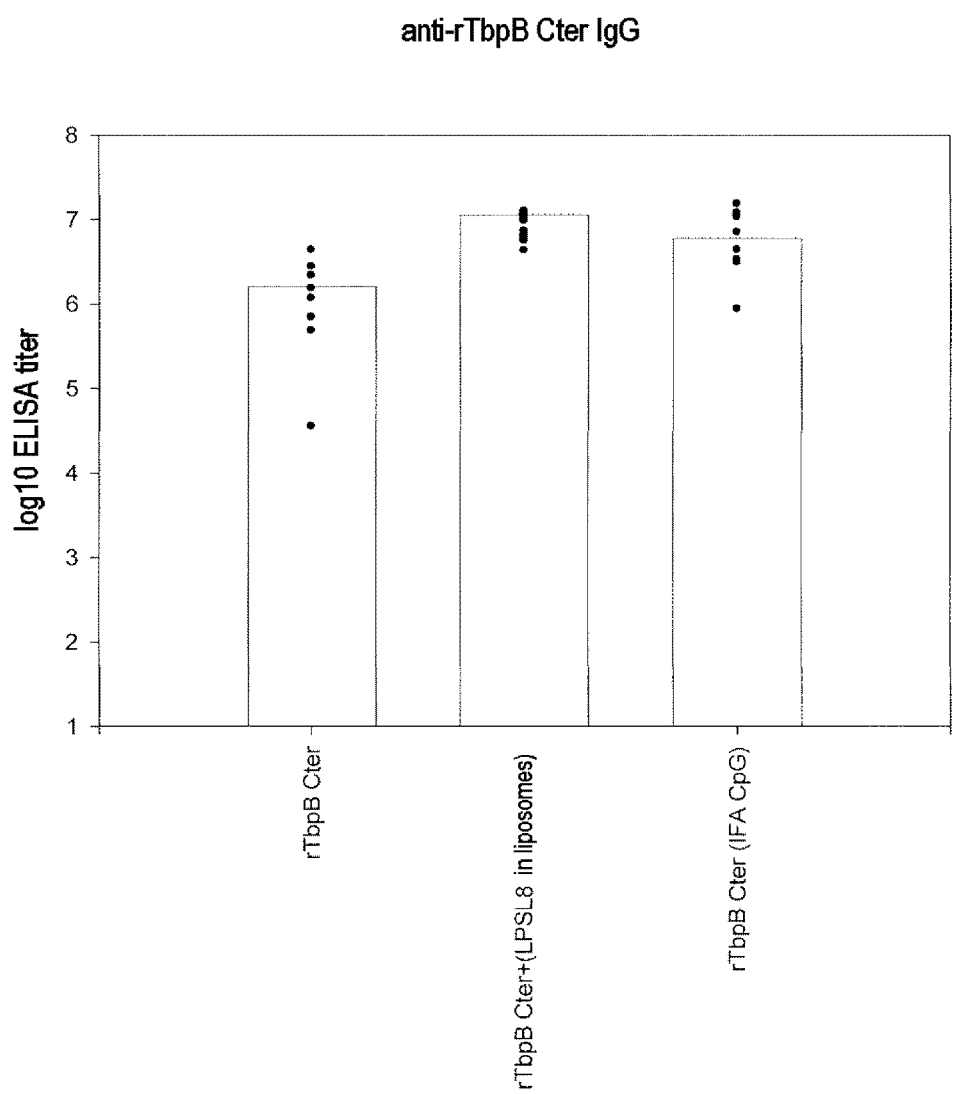

FIG. 7 gives the ELISA titers expressed as $\log_{10}$ of the anti-TbpB C-ter IgGs of the mouse sera.

FIGS. 8A and 8B give, respectively, the ELISA titers expressed as $\log_{10}$ of the anti-TbpB C-ter IgG1s and anti-TbpB C-ter IgG2as of the mouse sera.

The ELISA titers show that the lipidated rTbpB and the C-terminal region of TbpB (TbpB Cter, which is not lipidated) are strongly antigenic in rabbits just as they are in mice. On the other hand, only the lipidated rTbpB has a strong adjuvant effect on the LPS L8. This adjuvant effect is observed (i) when the lipidated rTbpB is simply mixed with [LPS L8] liposomes or (ii) when the lipidated rTbpB is mixed with LPS L8 and then the whole is formulated in liposomes; however, the latter embodiment gives slightly better results. The adjuvant effect of the lipidated rTbpB is also observed with the endotoxoid L8. In fact, in experiment No. 1 in the absence of lipidated rTbpB, the endotoxoid L8 produces effects similar to those of the [LPS L8] liposomes, while in experiment No. 2, the endotoxoid L8 mixed with lipidated rTbpB produces effects that are greater than those of the [LPS L8] liposomes and comparable to those of the [LPS L8] liposomes+lipidated rTbpB.

The LPS does not exhibit any adjuvant effect on the lipidated rTbpB probably due to a "plateau" effect specific to this antigen.

Bactericidal Activity Test (Rabbit Sera)

In experiments Nos. 1 and 2, the rabbit sera were tested with respect to the RH873 strain (strain of immunotype L8, isotype TbpB II) cultured in the presence and absence of Desferal, and to the M982 strain (strain of immunotype L3, isotype TbpB II) cultured in the presence of Desferal. The results are given in the tables below:

TABLE NO. 1

Experiment No. 1 - Detailed analysis of the rabbit sera of which samples were taken at D42: Bactericidal titers

| Immunization group | NZ KBL rabbit # | Sample | *N. meningitidis* B RH873 BHI + 50 μM desferal 2H30 | BHI + 50 μM desferal 4H00 | BHI 4H00 | *N. meningitidis* B M982 BHI + 50 μM desferal 2H30 |
|---|---|---|---|---|---|---|
| Group 3 | 5 | D-7 | <4 | | | [32] |
| Endotoxoid LPS L8 | | D42 | 8 | | | [32] |
| 40 μg | 6 | D-7 | <4 | | | [32] |
| | | D42 | <4 | | | [16] |
| | 7 | D-7 | <4 | | | [64] |
| | | D42 | [4] | | | [64] |
| | 8 | D-7 | [4] | | | [32] |
| | | D42 | [4] | | | [16] |
| Group 4 | 9 | D-7 | <4 | | | [8] |
| [LPS L8] liposome | | D42 | <4 | | | [16] |
| 40 μg | 10 | D-7 | <4 | | | [64] |
| | | D42 | 16 | | | [64] |
| Group 4 | 11 | D-7 | <4 | | | [32] |
| [LPS L8] liposome | | D42 | [8] | | | [64] |
| 40 μg | 12 | D-7 | 4 | | | 64 |
| | | D42 | [4] | | | [32] |
| Group 5 | 13 | D-7 | <4 | [4] | <4 | [32] |
| [rTbpB M982 + LPS L8] | | D42 | 64 | 256 | 64 | 256 |
| liposome | 14 | D-7 | <4 | [4] | <4 | [16]-[16] |
| 40 μg + 40 μg | | D42 | 128 | ≧2048 | 512 | 1024-2048 |
| | 15 | D-7 | <4 | [4] | [4] | [32]-[8] |
| | | D42 | 256 | 512 | 64 | ≧2048-2048 |
| | 16 | D-7 | <4 | [4] | <4 | [64] |
| | | D42 | 256 | 512 | 128 | 512 |
| Group 6 | 17 | D-7 | <4 | [4] | <4 | [64]-[16] |
| rTbpB M982 | | D42 | [4] | 8 | [4] | 1024-2048 |
| 40 μg | 18 | D-7 | <4 | [8] | [4] | [64]-[32] |
| | | D42 | 8 | 32 | <4 | 1024-1024 |

TABLE NO. 1-continued

Experiment No. 1 - Detailed analysis of the rabbit sera of which samples were taken at D42: Bactericidal titers

| Immunization group | NZ KBL rabbit # | Sample | N. meningitidis B RH873 BHI + 50 µM desferal 2H30 | BHI + 50 µM desferal 4H00 | BHI 4H00 | N. meningitidis B M982 BHI + 50 µM desferal 2H30 |
|---|---|---|---|---|---|---|
| Group 6 | 19 | D-7 | <4 | [4] | [4] | [32]-[64] |
| rTbpB M982 |  | D42 | 8 | 8 | [4] | ≧2048-1024 |
| 40 µg | 20 | D-7 | <4 | <4 | <4 | [128]-[16] |
|  |  | D42 | 32 | 128 | [4] | ≧2048-1024 |
| Group 7 | 21 | D-7 | <4 | [4] | <4 | [512]-[8] |
| rTbpB M982 + [LPS L8] |  | D42 | 64 | 256 | 32 | ≧2048-1024 |
| liposome | 22 | D-7 | <4 | [4] | <4 | [64]-[8] |
| 40 µg + 40 µg |  | D42 | 128 | 1024 | 32 | ≧2048-1024 |
|  | 23 | D-7 | <4 | [8] | <4 | [128]-[8] |
|  |  | D42 | 128 | 512 | 32 | >2048-1024 |
|  | 24 | D-7 | <4 | [4] | <4 | [256]-8 |
|  |  | D42 | 512 | 1024 | 256 | >2048-1024 |
| Group 1 | 1 | D-7 | <4 |  |  | [32] |
| Control buffer |  | D42 | <4 |  |  | 128 |
| Tris NaCl TWEEN pH 7.4 | 2 | D-7 | <4 |  |  | [32] |
|  |  | D42 | <4 |  |  | [32] |
| Group 2 | 3 | D-7 | <4 | <4 | <4 | [16] |
| Control liposome |  | D42 | <4 | [4] | <4 | [32] |
| Tris NaCl pH 7.4 | 4 | D-7 | <4 | <4 | <4 | [16] |
|  |  | D42 | <4 | [4] | <4 | [32] |

TABLE 2

Experiment No. 1 - Summary of results

| Immunization group | Bactericidal activity data | RH873 BHI + 50 µM desferal 2H30 | RH873 BHI 4H00 | M982 BHI + 50 µM desferal 2H30 |
|---|---|---|---|---|
| Group 3 Endotoxoid L8 | GMT and % of responders exhibiting a bactericidal titer ratio at D42/D-7 ≧ 4 | 4 (25%) | ND | 27 (0%) |
|  | Seroconversion at D42 (compared with D-7) | x 1.7 | ND | x 0.7 |
| Group 4 [LPS L8] liposome | GMT and % of responders exhibiting a bactericidal titer ratio at D42/D-7 ≧ 4 | 5.6 (50%) | ND | 38 (0%) |
|  | Seroconversion at D42 (compared with D-7) | x 2.3 | ND | x 1.2 |
| Group 5 [rTbpB M982 + LPS L8] liposome | GMT and % of responders exhibiting a bactericidal titer ratio at D42/D-7 ≧ 4 | 152 (100%) | 128 (100%) | 724 (100%) |
|  | Seroconversion at D42 (compared with D-7) | x 76 | x 56 | x 27 |
| Group 6 rTbpB M982 | GMT and % of responders exhibiting a bactericidal titer ratio at D42/D-7 ≧ 4 | 9.5 (75%) | 3.3 (0%) | 1448 (100%) |
|  | Seroconversion at D42 (compared with D-7) | x 4.7 | x 1.2 | x 23 |
| Group 7 rTbpB M982 + [LPS L8] liposome | GMT and % of responders exhibiting a bactericidal titer ratio at D42/D-7 is ≧ 4 | 152 (100%) | 54 (100%) | 2896 (100%) |
|  | Seroconversion at D42 (compared with D-7) | x 76 | x 27 | x 16 |
| Group 1 Buffer Tris NaCl TWEEN | GMT and % of responders exhibiting a bactericidal titer ratio at D42/D-7 ≧ 4 | 2 (0%) | ND | 64 (0%) |
|  | Seroconversion at D42 (compared with D-7) | x 1 | ND | x 2 |
| Group 2 Buffer Liposome | GMT and % of responders exhibiting a bactericidal titer ratio at D42/D-7 ≧ 4 | 2 (0%) | 2 (0%) | 32 (0%) |
|  | Seroconversion at D42 (compared with D-7) | x 1 | x 2 | x 2 |

Bactericidal activity of the antibodies with respect to the M982 strain is observed in all the groups having received rTbpB M982. This confirms that rTbpB has an intrinsic bactericidal activity against the homologous strain.

Considerable bactericidal activity of the antibodies with respect to the RH873 strain is also observed in the 2 groups having received proteosomes or rTbpB as a mixture with LPS L8 liposomes. The fact that the bactericidal titer of the "TbpB M982 alone" group is weak with respect to RH873 and that the bactericidal titers observed with respect to the RH873 strain cultured in the absence of Desferal (no expression of TbpB) are barely different from those obtained in chelated medium (expression of TbpB), reveals that the bactericidal activity observed with respect to this strain is due in large part to anti-LPS L8 antibodies and that the presence of rTbpB M982 (integrated or not integrated in liposomes) makes it possible to adjuvant the anti-LPS L8 response.

TABLE 3

Experiment No. 2 - Summary of results

| Immunization group | Bactericidal activity data | RH873 BHI + 50 μM desferal 2H30 | RH873 BHI 4h00 | M982 BHI + 50 μM desferal 2H30 |
|---|---|---|---|---|
| [LPS L8] liposomes + rTbpB (40 μg) | GMT and % of responders exhibiting a bactericidal titer ratio at D56/D-2 ≧ 4 | 152 (100%) | 54 (100%) | 2896 (100%) |
| | Seroconversion at D56 (compared with D-2) | x 63 | x 16 | x 256 |
| [LPS L8] liposomes + rTbpB (10 μg) | GMT and % of responders exhibiting a bactericidal titer ratio at D56/D-2 ≧ 4 | 181 (100%) | 108 (100%) | 3444 (100%) |
| | Seroconversion at D56 (compared with D-2) | x 65 | x 27 | x 305 |
| [LPS L8] liposomes + rTbpB (2.5 μg) | GMT and % of responders exhibiting a bactericidal titer ratio at D56/D-2 ≧ 4 | 181 (100%) | 128 (100%) | 2896 (100%) |
| | Seroconversion at D56 (compared with D-2) | x 75 | x 27 | x 305 |
| Endotoxoid LPS L8 + rTbpB (40 μg) | GMT and % of responders exhibiting a bactericidal titer ratio at D56/D-2 ≧ 4 | 181 (100%) | 152 (100%) | 2896 (100%) |
| | Seroconversion at D56 (compared with D-2) | x 75 | x 45 | x 256 |
| [LPS L8] liposomes | GMT and % of responders exhibiting a bactericidal titer ratio at D56/D-2 ≧ 4 | 22.7 (100%) | 38 (100%) | 23 (0%) |
| | Seroconversion at D56 (compared with D-2) | x 8.1 | x 11 | x 1.4 |
| Empty liposomes | GMT and % of responders exhibiting a bactericidal titer ratio at D56/D-2 ≧ 4 | 4 (0%) | 4 (0%) | 16 (0%) |
| | Seroconversion at D56 (compared with D-2) | x 2 | x 2 | x 1.4 |

The results obtained in experiment No. 2 confirm those already obtained: namely the demonstration of the adjuvant effect of rTbpB (data not provided). In rabbits, this effect is already at a maximum at the dose of 2.5 μg. The adjuvant effect is also exerted on the endotoxoid.

What is claimed is:

1. A method of making a preparation comprising the lipopolysaccharide (LPS) of a Gram-negative bacterium, the method comprising:

(i) mixing the LPS or the LPS formulated in liposomes (LPS liposomes) with the lipidated human-transferrin receptor subunit B protein (TbpB) of *Neisseria meningitidis* or a lipidated fragment thereof that comprises one or more T-helper epitopes;

(ii) formulating the LPS and the lipidated TbpB of *N. meningitidis* or the lipidated fragment thereof together in liposomes; or (iii) conjugating the LPS with the lipidated TbpB of *N. meningitidis* or the lipidated fragment thereof;

wherein the mixing, the formulating, or the conjugating yields a preparation which does not contain outer membrane vesicles (OMVs).

2. The method as claimed in claim 1, wherein the LPS is the lipooligosaccharide (LOS) of *N. meningitidis*.

3. The method as claimed in claim 1, wherein the LPS is detoxified and (i) the detoxified LPS is mixed with the TbpB of *N. meningitidis* or the lipidated fragment; or (ii) the detoxified LPS is conjugated with the lipidated TbpB of *N. meningitidis* or the lipidated fragment.

4. The method as claimed in claim 1, the method comprising (i) mixing the LPS liposomes with the lipidated TbpB of *N. meningitidis* or the lipidated fragment; or (ii) mixing the LPS and the lipidated TbpB of *N. meningitidis* or the lipidated fragment to form liposomes.

5. The method as claimed in claim 4, in which the liposomes are made up of a mixture of cationic and neutral lipids.

6. The method as claimed in claim 3, wherein the LPS is the LOS of *N. meningitidis*.

7. The method as claimed in claim 4, wherein the LPS is the LOS of *N. meningitidis*.

8. The method as claimed in claim 5, wherein the LPS is the LOS of *N. meningitidis*.

* * * * *

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Ser or Ala
<220> FEATURE:
<221> NAME/KEY: MISC_FEATURE
<222> LOCATION: (3)..(3)
```

-continued

```
<223> OTHER INFORMATION: Xaa is Ala or Gly

<400> SEQUENCE: 1

Leu Xaa Xaa Cys
1

<210> SEQ ID NO 2
<211> LENGTH: 20
<212> TYPE: PRT
<213> ORGANISM: Artificial Sequence
<220> FEATURE:
<223> OTHER INFORMATION: Synthetic

<400> SEQUENCE: 2

Met Lys Ala Thr Lys Leu Val Leu Gly Ala Val Ile Leu Gly Ser Thr
1               5                   10                  15

Leu Leu Ala Gly
            20

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Lys Thr Lys Cys Lys Phe Leu Leu Leu Cys
1               5                   10

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
tccatgacgt tcctgacgtt                                                  20
```